US008032224B2

(12) United States Patent
Miesel et al.

(10) Patent No.: US 8,032,224 B2
(45) Date of Patent: *Oct. 4, 2011

(54) SENSITIVITY ANALYSIS FOR SELECTING THERAPY PARAMETER SETS

(75) Inventors: Keith A. Miesel, St. Paul, MN (US); Kenneth T. Heruth, Edina, MN (US); Jonathan C. Werder, Corcoran, MN (US); Steve R. LaPorte, San Antonio, TX (US); Nina M. Graves, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 1130 days.

This patent is subject to a terminal disclaimer.

(21) Appl. No.: 11/691,413

(22) Filed: Mar. 26, 2007

(65) Prior Publication Data
US 2008/0071324 A1 Mar. 20, 2008

Related U.S. Application Data

(63) Continuation-in-part of application No. 11/081,873, filed on Mar. 16, 2005, now Pat. No. 7,542,803, application No. 11/691,413.

(60) Provisional application No. 60/553,769, filed on Mar. 16, 2004, provisional application No. 60/785,597, filed on Mar. 24, 2006.

(51) Int. Cl.
*A61N 1/34* (2006.01)
*A61N 1/36* (2006.01)
(52) U.S. Cl. .......................................... 607/46; 600/300
(58) Field of Classification Search .................. None
See application file for complete search history.

(56) References Cited

U.S. PATENT DOCUMENTS

| 4,297,685 A | 10/1981 | Brainard, II |
| 4,550,736 A | 11/1985 | Broughton et al. |
| 4,771,780 A | 9/1988 | Sholder |
| 4,776,345 A | 10/1988 | Cohen et al. |
| 4,846,195 A | 7/1989 | Alt |
| 5,040,536 A | 8/1991 | Riff |
| 5,058,584 A | 10/1991 | Bourgeois |
| 5,125,412 A | 6/1992 | Thornton |

(Continued)

FOREIGN PATENT DOCUMENTS
DE 198 31 109 1/2000
(Continued)

OTHER PUBLICATIONS

Office Action dated Nov. 7, 2007 for U.S. Appl. No. 11/081,873 (7 pgs.).

(Continued)

*Primary Examiner* — Carl H. Layno
*Assistant Examiner* — Jon-Eric C. Morales
(74) *Attorney, Agent, or Firm* — Shumaker & Sieffert, P.A.

(57) ABSTRACT

Techniques for controlling delivery of a therapy to a patient by a medical device, such as an implantable medical device (IMD), involve a sensitivity analysis of a performance metric. The performance metric may relate to efficacy or side effects of the therapy. For example, the performance metric may comprise a sleep quality metric, an activity level metric, a movement disorder metric for patients with Parkinson's disease, epilepsy, or the like. The sensitivity analysis identifies values of therapy parameters that defines a substantially maximum or minimum value of the performance metric. The identified therapy parameters are a baseline therapy parameter set, and a medical device may control delivery of the therapy based on the baseline therapy parameter set.

44 Claims, 11 Drawing Sheets

U.S. PATENT DOCUMENTS

| | | | |
|---|---|---|---|
| 5,154,180 | A | 10/1992 | Blanchet et al. |
| 5,233,984 | A | 8/1993 | Thompson |
| 5,275,159 | A | 1/1994 | Griebel |
| 5,335,657 | A | 8/1994 | Terry, Jr. et al. |
| 5,337,758 | A | 8/1994 | Moore et al. |
| 5,342,409 | A | 8/1994 | Mullett |
| 5,469,861 | A | 11/1995 | Piscopo et al. |
| 5,476,483 | A | 12/1995 | Bornzin et al. |
| 5,509,927 | A * | 4/1996 | Epstein et al. ............... 607/32 |
| 5,514,162 | A | 5/1996 | Bornzin et al. |
| 5,591,216 | A * | 1/1997 | Testerman et al. ............ 607/42 |
| 5,593,431 | A | 1/1997 | Sheldon |
| 5,622,428 | A | 4/1997 | Bonnet |
| 5,645,053 | A | 7/1997 | Remmers et al. |
| 5,683,432 | A * | 11/1997 | Goedeke et al. ............... 607/32 |
| 5,732,696 | A | 3/1998 | Rapoport et al. |
| 5,782,884 | A | 7/1998 | Stotts et al. |
| 5,814,093 | A | 9/1998 | Stein |
| 5,895,371 | A | 4/1999 | Levitas et al. |
| 5,904,708 | A * | 5/1999 | Goedeke ....................... 607/18 |
| 5,919,149 | A | 7/1999 | Allum |
| 5,938,690 | A * | 8/1999 | Law et al. ...................... 607/46 |
| 5,941,906 | A | 8/1999 | Barreras, Sr. et al. |
| 5,944,680 | A | 8/1999 | Christopherson et al. |
| 5,999,846 | A | 12/1999 | Pardey et al. |
| 6,044,297 | A | 3/2000 | Sheldon et al. |
| 6,045,513 | A | 4/2000 | Stone et al. |
| 6,059,576 | A | 5/2000 | Brann |
| 6,091,973 | A | 7/2000 | Colla et al. |
| 6,095,991 | A | 8/2000 | Krausman et al. |
| 6,102,874 | A | 8/2000 | Stone et al. |
| 6,120,467 | A | 9/2000 | Schallhorn |
| 6,128,534 | A | 10/2000 | Park et al. |
| 6,157,857 | A | 12/2000 | Dimpfel |
| 6,161,095 | A * | 12/2000 | Brown ............................ 705/2 |
| 6,165,143 | A | 12/2000 | van Lummel |
| 6,259,948 | B1 | 7/2001 | Florio et al. |
| 6,280,409 | B1 | 8/2001 | Stone et al. |
| 6,296,606 | B1 | 10/2001 | Goldberg et al. |
| 6,308,098 | B1 | 10/2001 | Meyer |
| 6,315,740 | B1 | 11/2001 | Singh |
| 6,351,672 | B1 | 2/2002 | Park et al. |
| 6,366,813 | B1 * | 4/2002 | DiLorenzo ..................... 607/45 |
| 6,416,471 | B1 | 7/2002 | Kumar et al. |
| 6,440,090 | B1 | 8/2002 | Schallhorn |
| 6,449,508 | B1 | 9/2002 | Sheldon et al. |
| 6,459,934 | B1 | 10/2002 | Kadhiresan |
| 6,466,821 | B1 | 10/2002 | Pianca et al. |
| 6,468,234 | B1 | 10/2002 | Van der Loos et al. |
| 6,514,218 | B2 | 2/2003 | Yamamoto |
| 6,539,249 | B1 | 3/2003 | Kadhiresan et al. |
| 6,574,507 | B1 | 6/2003 | Bonnet |
| 6,605,038 | B1 | 8/2003 | Teller et al. |
| 6,611,783 | B2 | 8/2003 | Kelly, Jr. et al. |
| 6,626,902 | B1 | 9/2003 | Kucharczyk et al. |
| 6,659,968 | B1 | 12/2003 | McClure |
| 6,687,538 | B1 | 2/2004 | Hrdlicka et al. |
| 6,731,984 | B2 | 5/2004 | Cho et al. |
| 6,752,766 | B2 | 6/2004 | Kowallik et al. |
| 6,773,404 | B2 | 8/2004 | Poezevera et al. |
| 6,819,956 | B2 | 11/2004 | DiLorenzo |
| 6,878,121 | B2 | 4/2005 | Krausman et al. |
| 6,881,192 | B1 | 4/2005 | Park |
| 6,884,596 | B2 | 4/2005 | Civelli et al. |
| 6,890,306 | B2 | 5/2005 | Poezevera |
| 6,928,324 | B2 | 8/2005 | Park et al. |
| 6,937,891 | B2 * | 8/2005 | Leinders et al. ................ 607/2 |
| 6,964,641 | B2 | 11/2005 | Cho et al. |
| 7,130,689 | B1 | 10/2006 | Turcott |
| 7,141,034 | B2 * | 11/2006 | Eppstein et al. ............... 604/22 |
| 7,162,304 | B1 | 1/2007 | Bradley |
| 7,209,787 | B2 | 4/2007 | DiLorenzo |
| 7,542,803 | B2 * | 6/2009 | Heruth et al. .................. 607/46 |
| 2001/0031930 | A1 | 10/2001 | Roizen et al. |
| 2001/0037067 | A1 | 11/2001 | Tchou et al. |
| 2001/0041831 | A1 * | 11/2001 | Starkweather et al. ....... 600/365 |
| 2002/0077562 | A1 * | 6/2002 | Kalgren et al. ................ 600/510 |
| 2002/0091308 | A1 | 7/2002 | Kipshidze et al. |
| 2002/0161412 | A1 | 10/2002 | Sun et al. |
| 2002/0169485 | A1 | 11/2002 | Pless et al. |
| 2002/0177882 | A1 | 11/2002 | DiLorenzo |
| 2002/0193697 | A1 | 12/2002 | Cho et al. |
| 2002/0193839 | A1 | 12/2002 | Cho et al. |
| 2003/0004423 | A1 | 1/2003 | Lavie et al. |
| 2003/0139692 | A1 | 7/2003 | Barrey et al. |
| 2003/0149457 | A1 | 8/2003 | Tcheng et al. |
| 2003/0153953 | A1 * | 8/2003 | Park et al. ...................... 607/17 |
| 2003/0153955 | A1 | 8/2003 | Park et al. |
| 2003/0153956 | A1 | 8/2003 | Park et al. |
| 2003/0163059 | A1 | 8/2003 | Poezevera et al. |
| 2003/0171791 | A1 * | 9/2003 | KenKnight et al. ............ 607/60 |
| 2003/0195588 | A1 * | 10/2003 | Fischell et al. ................. 607/55 |
| 2003/0212445 | A1 | 11/2003 | Weinberg |
| 2004/0002741 | A1 | 1/2004 | Weinberg |
| 2004/0002742 | A1 | 1/2004 | Florio |
| 2004/0015103 | A1 | 1/2004 | Aminian et al. |
| 2004/0049132 | A1 | 3/2004 | Barron et al. |
| 2004/0077995 | A1 * | 4/2004 | Ferek-Petric et al. .......... 604/66 |
| 2004/0102814 | A1 | 5/2004 | Sorensen et al. |
| 2004/0111040 | A1 | 6/2004 | Ni et al. |
| 2004/0111041 | A1 | 6/2004 | Ni et al. |
| 2004/0220621 | A1 * | 11/2004 | Zhou et al. ....................... 607/2 |
| 2005/0021103 | A1 | 1/2005 | DiLorenzo |
| 2005/0021104 | A1 | 1/2005 | DiLorenzo |
| 2005/0042589 | A1 | 2/2005 | Hatlestad et al. |
| 2005/0060001 | A1 | 3/2005 | Singhal et al. |
| 2005/0113710 | A1 | 5/2005 | Stahmann et al. |
| 2005/0119703 | A1 | 6/2005 | DiLorenzo |
| 2005/0177192 | A1 | 8/2005 | Rezai et al. |
| 2005/0209511 | A1 | 9/2005 | Heruth et al. |
| 2005/0209512 | A1 | 9/2005 | Heruth et al. |
| 2005/0209513 | A1 | 9/2005 | Heruth et al. |
| 2005/0209643 | A1 | 9/2005 | Heruth et al. |
| 2005/0209644 | A1 | 9/2005 | Heruth et al. |
| 2005/0209645 | A1 | 9/2005 | Heruth et al. |
| 2005/0215847 | A1 | 9/2005 | Heruth et al. |
| 2005/0215947 | A1 | 9/2005 | Heruth et al. |
| 2005/0216064 | A1 | 9/2005 | Heruth et al. |
| 2005/0222522 | A1 | 10/2005 | Heruth et al. |
| 2005/0222626 | A1 | 10/2005 | DiLorenzo |
| 2005/0222643 | A1 | 10/2005 | Heruth et al. |
| 2005/0234514 | A1 | 10/2005 | Heruth et al. |
| 2005/0234518 | A1 | 10/2005 | Heruth et al. |
| 2005/0240086 | A1 | 10/2005 | Akay |
| 2005/0240242 | A1 | 10/2005 | DiLorenzo |
| 2005/0245790 | A1 | 11/2005 | Bergfalk et al. |
| 2005/0245988 | A1 | 11/2005 | Miesel |
| 2006/0224191 | A1 | 10/2006 | DiLorenzo |
| 2006/0293720 | A1 | 12/2006 | DiLorenzo |
| 2007/0073355 | A1 | 3/2007 | DiLorenzo |
| 2007/0142862 | A1 | 6/2007 | DiLorenzo |

FOREIGN PATENT DOCUMENTS

| | | |
|---|---|---|
| DE | 100 24 103 | 11/2001 |
| EP | 0 564 803 A1 | 10/1993 |
| EP | 0 849 715 B1 | 6/1998 |
| EP | 1 195 139 A1 | 4/2002 |
| EP | 1 291 036 A2 | 3/2003 |
| EP | 1 308 182 A2 | 5/2003 |
| EP | 1 437 159 A1 | 7/2004 |
| EP | 1 322 227 B1 | 12/2005 |
| GB | 2 330 912 A | 5/1999 |
| WO | WO 98/00197 | 1/1998 |
| WO | WO 99/13765 | 3/1999 |
| WO | WO 01/37930 | 5/2001 |
| WO | WO 02/28282 | 4/2002 |
| WO | WO 02/41771 | 5/2002 |
| WO | WO 02/087433 | 11/2002 |
| WO | WO 02/096512 | 12/2002 |
| WO | WO 02/100267 | 12/2002 |
| WO | WO 03/024325 | 3/2003 |
| WO | WO 03/051356 | 6/2003 |
| WO | WO 03/065891 | 8/2003 |
| WO | WO 2005/028029 | 3/2005 |
| WO | WO 2005/035050 | 4/2005 |

OTHER PUBLICATIONS

Office Action dated Oct. 14, 2009 for U.S. Appl. No. 11/081,857 (14 pgs.).
Response dated Dec. 14, 2009 for U.S. Appl. No. 11/081,857 (8 pgs.).
Advisory Action dated Jan. 12, 2010 for U.S. Appl. No. 11/081,857 (3 pgs.).
Office Action dated Nov. 6, 2008 for U.S. Appl. No. 11/081,857 (8 pgs.).
Response dated Jan. 6, 2009 for U.S. Appl. No. 11/081,857 (6 pgs.).
Office Action dated Nov. 19, 2008 for U.S. Appl. No. 11/796,811 (7 pgs.).
Response dated Feb. 12, 2009 for U.S. Appl. No. 11/081,155 (7 pgs.).
Responsive Amendment dated Feb. 19, 2009 for U.S. Appl. No. 11/796,811 (15 pgs.).
Office Action dated Dec. 12, 2008 for U.S. Appl. No. 11/081,811 (12 pgs.).
Responsive Amendment dated Mar. 12, 2009 for U.S. Appl. No. 11/081,811 (13 pgs.).
Office Action dated Apr. 10, 2008 for U.S. Appl. No. 11/081,873 (6 pgs.).
Responsive Amendment dated Jun. 10, 2008 for U.S. Appl. No. 11/081,873 (8 pgs.).
Office Action dated May 5, 2008 for U.S. Appl. No. 10/826,925 (12 pgs.).
Office Action dated May 30, 2008 for U.S. Appl. No. 11/081,811 (13 pgs.).
Office Action dated Apr. 23, 2008 for U.S. Appl. No. 11/796,811 (6 pgs.).
Office Action dated May 6, 2008 for U.S. Appl. No. 10/825,955 (13 pgs.).
Response to Office Action dated Jul. 2, 2008 for U.S. Appl. No. 10/825,955 (13 pgs.).
Office Action dated May 9, 2008 for U.S. Appl. No. 11/081,857 (10 pgs.).
Office Action dated Apr. 4, 2008 for U.S. Appl. No. 11/081,155 (9 pgs.).
Amzica, "Physiology of Sleep and Wakefulness as it Relates to the Physiology of Epilepsy," Journal of Clinical Neurophysiology, American Clinical Neurophysiology Society, 19(6), pp. 488-503, (2002).
Dinner, "Effect of Sleep on Epilepsy," Journal of Clinical Neurophysiology, American Clinical Neurophysiology Society, 19(6), pp. 504-513, (2002).
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, (2002).
Mendez et al. "Interactions Between Sleep and Epilepsy," Journal of Clinical Neurophysiology, American Clinical Neurophysiology Society, 18(2), pp. 106-127, (2001).
"MiniMitter® Physiological and Behavioral Monitoring for Humans and Animals," http://www.minimitter.com/Products/Actiwatch, 3 pgs. Feb. 20, 2006.
"IBM & Citzen Watch develop Linux-based 'WatchPads'," 5 pgs., http://www.linuxdevices.com/news/NS6580187845.html, Feb. 20, 2006.
"Design Competition: Runners-Up for the Best Three Designs," EPN, vol. 26, No. 1, 1 pg., (2002).
"Watch," Wikipedia, the free encyclopedia, 6 pgs., http://en.wikipedia.org/wiki/Watch, Feb. 20, 2006.
Kassam, "2005 EDP Topic 'MK4': Tremor Data-Logger for Parkinson's Disease Patients," http://www.ee.ryerson.ca/~courses/edp2005/MK4.html, 3 pgs., Feb. 20, 2006.
Tuisku, "Motor Activity Measured by Actometry in Neuropsychiatric Disorders," Department of Psychiatry, University of Helsinki, Helsinki, Finland, 115 pgs. (2002).
Smith et al., "Presleep Cognitions in Patients with Insomnia Secondary to Chronic Pain," Journal of Behavioral Medicine, vol. 24, No. 1, pp. 93-114, (2001).
Smith et al. "How do sleep disturbance and chronic pain inter-relate? Insights from the longitudinal and cognitive-behavioral clinical trials literature," Sleep Medicine Reviews, YSMRV 286, pp. 1-14, (2003).
Goodrich et al., "The Prediction of Pain Using Measures of Sleep Quality," Pain Digest, 8:23-25, (1998).
"Analysis of heart rate dynamics by methods derived from nonlinear mathematics: Clinical applicability and prognostic significance" http:/herkules.oulu.fi.isbn9514250133/html, 4 pgs., (2004).
Kerr et al., "Analysis of the sit-stand-sit movement cycle in normal subjects," Clinical Biomechanics, vol. 12, No. 4, pp. 236-245, (1997).
Aminian et al. "Physical Activity Monitoring Based on Accelerometry: Validation and Comparison with Video Observation," Medical & Biological Engineering & Computing, vol. 37, No. 2, pp. 304-308 (1999).
Medcare—A Global Leader in Sleep Diagnostics, Embletta Recording System, http://www.medcare.com/products/diagnostic/embletta/, 2 pgs. Jan. 31, 2005.
Medcare—A Global Leader in Sleep Diagnostics, Somnologica for Embletta, http://www.medcare.com/products/diagnostic/embletta/SomnoEmbletta/index.asp, 1 pg. Jan. 31, 2005.
Map Medizin-Technologie GmbH, Poly-MESAM®, http://195.244.124.130/map/de/eng/map_med.nsf/smsall/70564A3FCBE4188AC1256EF4.., 4 pgs. Jan. 31, 2005.
Merlin, http://www.aha.ru/~pir/english/merlin/, 4 pgs. Jan. 31, 2005.
Sleep Solutions—PR Newswire: Sleep Solutions Introduces NovaSom™ QSG™ for PSG.., http://www.sleep-solutions.com/press_room/novasom.htm, 2 pgs. Jan. 31, 2005.
Itamar Medical Information, http://itamar-medical.com/content.asp?id-id=31, 2 pgs. Jan. 31, 2005.
Criticare System Inc.,-504DX Portable Pulse Oximeter, http://www.csiusa.com/504dx.html, 4 pgs. Jan. 31, 2005.
Snaps® Laboratories, Product Fact Sheet, http://www.snaplab.com/mp_fact.htm, 2 pgs. Jan. 31, 2005.
Sleep Strip & Bite Strip, http://ww.quietsleep.com/snoringapnea/sleepstrip.htm, 8 pgs. Jan. 31, 2005.
"Bitestrip Flier," downloaded from Internet Archive of www.quietsleep.com dated Jan. 29, 2005 http://web.archive.org/web/20041124080003/www.quietsleep.com/pdf/Bitestrip+Flier.pdf.
"Bilateral Comparisons of the BiteStrip Bruxism Device and Masseter EMG Bruxism Events" downloaded from Internet Archive of www.quietsleep.com dated Jan. 29, 2005 http://web.archive.org/web/20041124075114/www.quietsleep.com/pdf/Bilateral+Comparisons.pdf.
"The BiteStrip: A Novel Screener for Sleep Bruxism," downloaded from Internet Archive of www.quietsleep.com dated Jan. 29, 2005 http://web.archive.org/web/20041124072922/www.quietsleep.com/pdf/BiteStrip-+Novel+Screener.pdf.
Office Action dated Jul. 20, 2006 for U.S. Appl. No. 10/825,955, filed Apr. 15, 2004, (10 pgs.).
Responsive Amendment dated Oct. 20, 2006 for U.S. Appl. No. 10/825,955, filed Apr. 15, 2004 (21 pgs.).
Office Action dated Jan. 17, 2007 for U.S. Appl. No. 10/825,955, filed Apr. 15, 2004, (10 pgs.).
Responsive Amendment dated Mar. 19, 2007 for U.S. Appl. No. 10/825,955, filed Apr. 15, 2004 (13 pgs.).
Office Action dated Jun. 27, 2007 for U.S. Appl. No. 10/825,955, filed Apr. 15, 2004, (13 pgs).
Office Action dated Jul. 5, 2006 for U.S. Appl. No. 10/825,953, filed Apr. 15, 2004, (11 pgs.).
Responsive Amendment dated Oct. 5, 2006 for U.S. Appl. No. 10/825,953, filed Apr. 15, 2004 (17 pgs.).
Office Action dated Dec. 28, 2006 for U.S. Appl. No. 10/825,953, filed Apr. 15, 2004, (9 pgs.).
Response dated Feb. 28, 2007 for U.S. Appl. No. 10/825,953, filed Apr. 15, 2004 (7 pgs.).
Office Action dated Apr. 3, 2007 for U.S. Appl. No. 10/825,953, filed Apr. 15, 2004, (8 pgs.).
Responsive Amendment dated Jun. 28, 2007 for U.S. Appl. No. 10/825,953, filed Apr. 15, 2004 (19 pgs.).
Office Action dated Jul. 3, 2007 for U.S. Appl. No. 10/826,925, filed Apr. 15, 2004, (22 pgs.).
Responsive Amendment dated Aug. 4, 2008 for U.S. Appl. No. 11/081,155 (12 pgs.).
Responsive Amendment dated Aug. 7, 2008 for U.S. Appl. No. 11/081,857 (13 pgs.).

Response dated Aug. 22, 2008 for U.S. Appl. No. 10/826,925 (7 pgs.).
Responsive Amendment dated Aug. 22, 2008 for U.S. Appl. No. 11/796,811 (13 pgs.).
Responsive Amendment dated Aug. 29, 2008 for U.S. Appl. No. 11/081,811 (13 pgs.).
Office Action dated Dec. 21, 2009 for U.S. Appl. No. 11/691,405 (11 pgs.).
Responsive Amendment dated Mar. 22, 2010 for U.S. Appl. No. 11/691,405 (18 pgs.).
Office Action dated Feb. 5, 2010 for U.S. Appl. No. 11/691,430 (12 pgs.).
Responsive Amendment dated Jun. 2, 2010 for U.S. Appl. No. 11/691,430 (15 pgs.).
Office Action dated May 20, 2010 for U.S. Appl. No. 12/248,622 (6 pgs.).
Responsive Amendment dated Aug. 5, 2010 for U.S. Appl. No. 12/248,622 (10 pgs.).
Request for Continued Examination and Amendment dated Aug. 19, 2010 for U.S. Appl. No. 11/691,405 (17 pgs.).
Advisory Action dated Oct. 12, 2010 for U.S. Appl. No. 12/351,414, (3 pgs.).
Office Action dated Aug. 2, 2010 for U.S. Appl. No. 12/351,414, (21 pgs.).
Response dated Oct. 1, 2010 for U.S. Appl. No. 12/351,414, (10 pgs.).
Office Action dated Aug. 5, 2010 for U.S. Appl. No. 12/248,609, (8 pgs.).
Office Action dated Apr. 22, 2010 for U.S. Appl. No. 11/691,423 (8 pgs.).
Responsive Amendment dated Jul. 22, 2010 for U.S. Appl. No. 11/691,423 (15 pgs.).
Office Action dated May 20, 2010 for U.S. Appl. No. 12/248,622 (6 pgs.).
Office Action dated Apr. 28, 2010 for U.S. Appl. No. 11/081,811 (18 pgs.).
Office Action dated May 19, 2010 for U.S. Appl. No. 11/691,405 (12 pgs.).
Request for Continued Examination and Amendment dated Jul. 28, 2010 for U.S. Appl. No. 11/081,811 (19 pgs.).
Responsive Amendment dated Nov. 4, 2010 for U.S. Appl. No. 12/248,609, (10 pgs.).
Office Action dated Dec. 22, 2010 for U.S. Appl. No. 12/248,609, (7 pgs.).
Advisory Action dated Feb. 28, 2011 for U.S. Appl. No. 12/248,609, (3 pgs.).
European Examination Report dated Mar. 26, 2010 for European Application No. 05732953.4 (4 pgs.).
Office Action dated Sep. 29, 2010 for U.S. Appl. No. 12/248,622, (7 pgs.).
Response dated Nov. 18, 2010 for U.S. Appl. No. 12/248,622, (10 pgs.).
Notice of Appeal and Pre-Appeal Brief Request for Review dated Mar. 22, 2011 for U.S. Appl. No. 12/248,609, (6 pgs.).
Office Action dated Feb. 17, 2011 for U.S. Appl. No. 11/691,405, (9 pgs.).
Responsive Amendment dated May 17, 2011 for U.S. Appl. No. 11/691,405, (14 pgs.).
Office Action dated May 10, 2011 for U.S. Appl. No. 12/248,622, (6 pgs.).
Responsive Amendment dated Aug. 10, 2011 for U.S. Appl. No. 12/248,622, (10 pgs.).
Office Action dated May 10, 2011 for U.S. Appl. No. 12/248,609, (7 pgs.).
Responsive Amendment dated Aug. 10, 2011 for U.S. Appl. No. 12/248,609, (11 pgs.).

* cited by examiner

SENSITIVITY ANALYSIS FOR SELECTING THERAPY PARAMETER SETS

This application is a continuation-in-part of U.S. application Ser. No. 11/081,873, filed Mar. 16, 2005, now U.S. Pat. No. 7,542,803 which claims the benefit of U.S. provisional application No. 60/553,769, filed Mar. 16, 2004. This application also claims the benefit of U.S. provisional application No. 60/785,597, filed Mar. 24, 2006. The entire content of each of these applications is incorporated herein by reference.

TECHNICAL FIELD

The invention relates to medical devices and, more particularly, to medical devices that deliver a therapy.

BACKGROUND

In some cases, an ailment may affect a patient's sleep quality or physical activity level, or a therapy delivered to the patient to treat the ailment may produce undesirable side effects. For example, chronic pain may cause a patient to have difficulty falling asleep, and may disturb the patient's sleep, e.g., causing the patient to wake. Further, chronic pain may cause the patient to have difficulty achieving deeper sleep states, such as one of the nonrapid eye movement (NREM) sleep states associated with deeper sleep. Other ailments that may negatively affect patient sleep quality include movement disorders, such as tremor, Parkinson's disease, multiple sclerosis, epilepsy, or spasticity, as well as psychological disorders, such as depression, mania, bipolar disorder, or obsessive-compulsive disorder. Further, sleep apnea, congestive heart failure, gastrointestinal disorders and incontinence may negatively affect patient sleep quality. As another example, chronic pain may cause a patient to avoid particular physical activities, or activity in general, where such activities increase the pain experienced by the patient. Neurological disorders such as movement disorders and psychological disorders, in addition to congestive heart failure, may also affect patient activity level.

Furthermore, in some cases, poor sleep quality may increase the symptoms experienced by a patient due to an ailment. For example, poor sleep quality has been linked to increased pain symptoms in chronic pain patients, increased tremor or other inappropriate movements in movement disorder patients, and worsening of psychological symptoms. The link between poor sleep quality and increased symptoms is not limited to ailments that negatively impact sleep quality, such as those listed above. Nonetheless, the condition of a patient with such an ailment may progressively worsen when symptoms disturb sleep quality, which in turn increases the frequency and/or intensity of symptoms.

In some cases, these ailments are treated via a medical device, such as an implantable medical device (IMD). For example, patients may receive an implantable neurostimulator or drug delivery device to treat chronic pain or a movement disorder. Congestive heart failure may be treated by, for example, a cardiac pacemaker or drug delivery device.

SUMMARY

In general, the invention is directed to techniques for controlling delivery of a therapy to a patient by a medical device, such as an implantable medical device (IMD), based on a sensitivity analysis of a performance metric. The performance metric may relate to efficacy or side effects associated with a particular therapy. For example, the performance metric may comprise a sleep quality metric, an activity level metric, a posture metric, a movement disorder metric for patients with Parkinson's disease, a side-effects metric, or the like. The sensitivity analysis facilitates determination of a therapy parameter set that defines a substantially maximum or minimum value of the performance metric. A medical device according to an embodiment of the invention may conduct the sensitivity analysis for the performance metric, and identify values for each of a plurality of physiological parameters based on the sensitivity analysis. A system according to an embodiment of the invention may include a monitor, a programmer, and a therapy device to conduct the sensitivity analysis for the performance metric, and determine a baseline therapy parameter set based on the sensitivity analysis. In either case, the medical device or another medical device may control delivery of the therapy based on a baseline therapy parameter set that includes the identified values. The baseline therapy parameter set may be a therapy parameter set found to be most efficacious or to result in the least side effects, as indicated by the performance metric value associated with that therapy parameter set.

For the sensitivity analysis, a medical device may deliver therapy according to a plurality of different therapy parameter sets encompassing a range of therapy parameter values. The therapy parameter sets may be generated either randomly or non-randomly. The therapy parameter sets may be defined, for example, by the medical device or an external programming device. The medical device, programming device, or another device may monitor performance metric values for each therapy parameter set in order to conduct the sensitivity analysis.

Furthermore, after a baseline therapy parameter set has been identified, the medical device that delivers therapy according to the baseline therapy parameter set may periodically perturb at least one therapy parameter value of the baseline therapy parameter set to determine whether the performance metric value has changed over time. The therapy parameter may be increased or decreased in small increments relative to the range values. If perturbing the therapy parameter improves the performance metric, the therapy parameter value is further increased or decreased to again define a substantially maximum or minimum performance metric value. The baseline therapy parameter set is then updated to correspond to the therapy parameter set with the perturbed therapy parameter value or values. If changing the therapy parameter worsens the performance metric, the baseline therapy parameter set is maintained. The medical device that delivers therapy according to the baseline therapy parameter set, a programming device, or another device may determine the performance metric values for each perturbation, and update the baseline therapy parameter set if indicated by the comparison to the performance metric value for the baseline therapy parameter set.

The therapy may be directed to treating any number of disorders. For example, the therapy may be directed to treating a non-respiratory neurological disorder, such as a movement disorder or psychological disorder. Example movement disorders for which therapy may be provided are Parkinson's disease, essential tremor and epilepsy. Non-respiratory neurological disorders do not include respiratory disorders, such as sleep apnea.

The medical device or a separate monitor, as examples, may monitor one or more physiological parameters of the patient in order to determine values for the one or more performance metrics. Example physiological parameters that the medical device may monitor include activity level, posture, heart rate, ECG morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response. These parameters may be indicative of sleep quality and activity level, and therefore may be useful in determining the performance metric values for different therapy parameter sets. In some embodiments, the medical device additionally or alternatively monitors the variability of one or more of these parameters. In order to monitor one or more of these parameters, the medical device may include, be coupled to, or be in wireless communication with one or more sensors, each of which outputs a signal as a function of one or more of these physiological parameters.

In one embodiment, the invention is directed to a method comprising delivering a therapy to a patient via a medical device according to each of a plurality of therapy parameter sets, each of the parameter sets including a value for each of a plurality of therapy parameters, and monitoring a value of a performance metric of a patient for each of a plurality of therapy parameter sets. The method further comprises conducting a sensitivity analysis of the performance metric for each of the plurality of therapy parameter sets, and identifying a value for each of the therapy parameters based on the sensitivity analysis.

In another embodiment, the invention is directed to a medical device that includes a therapy module and a processor. The therapy module delivers a therapy to a patient according to each of a plurality of therapy parameter sets, each of the therapy parameter sets including a value for each of a plurality of therapy parameters. The processor monitors a value of a performance metric of the patient for each of a plurality of therapy parameter sets. The processor further conducts a sensitivity analysis of the performance metric for each of the plurality of therapy parameter sets, and identifies a value for each of the therapy parameters based on the sensitivity analysis.

In another embodiment, the invention is directed to a computer-readable medium containing instructions. The instructions cause a programmable processor to monitor a value of a performance metric of a patient for each of a plurality of therapy parameter sets, wherein a medical device delivers a therapy to the patient according to each of the therapy parameters sets, and each of the parameter sets includes a value for each of a plurality of therapy parameters. The instructions further cause the processor to conduct a sensitivity analysis of the performance metric for each of the plurality of therapy parameter sets, and identify a value for each of the plurality of therapy parameters based on the sensitivity analysis.

In another embodiment, the invention is directed to a system comprising a therapy device, a monitor, and a computing device. The therapy device delivers therapy to a patient according to each of a plurality of therapy parameter sets, each of the therapy parameter sets including a value for each of a plurality of therapy parameters. The monitor monitors values of at least one physiological parameter of a patient for each of the plurality of therapy parameter sets. The computing device receives the physiological parameter values from the monitor, identifies values of a performance metric of the patient for each of the plurality of parameter sets based on the physiological parameter values, conducts a sensitivity analysis of the performance metric for each of the plurality of therapy parameter sets, and identifies a value for each of the therapy parameters based on the sensitivity analysis.

The invention is capable of providing one or more advantages. For example, through the sensitivity analysis of the performance metric, a baseline therapy parameter set that provides substantially maximum or minimum value of the performance metric may be identified. A medical device may provide therapy according to the baseline therapy parameter set.

Further, the medical device may be able to adjust therapy to produce an improved performance metric value. In particular, the adjustments may address symptoms that cause a poor performance metric value or symptoms that are worsened by a poor performance metric value. Adjusting therapy based on the performance metric value information may significantly improve the patient's performance quality and condition. The ability of a medical device to periodically check performance metric values and adjust therapy parameters based on the performance metric values may reduce the need for the patient to make time consuming and expensive clinic visits when the patient's sleep is disturbed, physical activity level has decreased, or symptoms have worsened.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
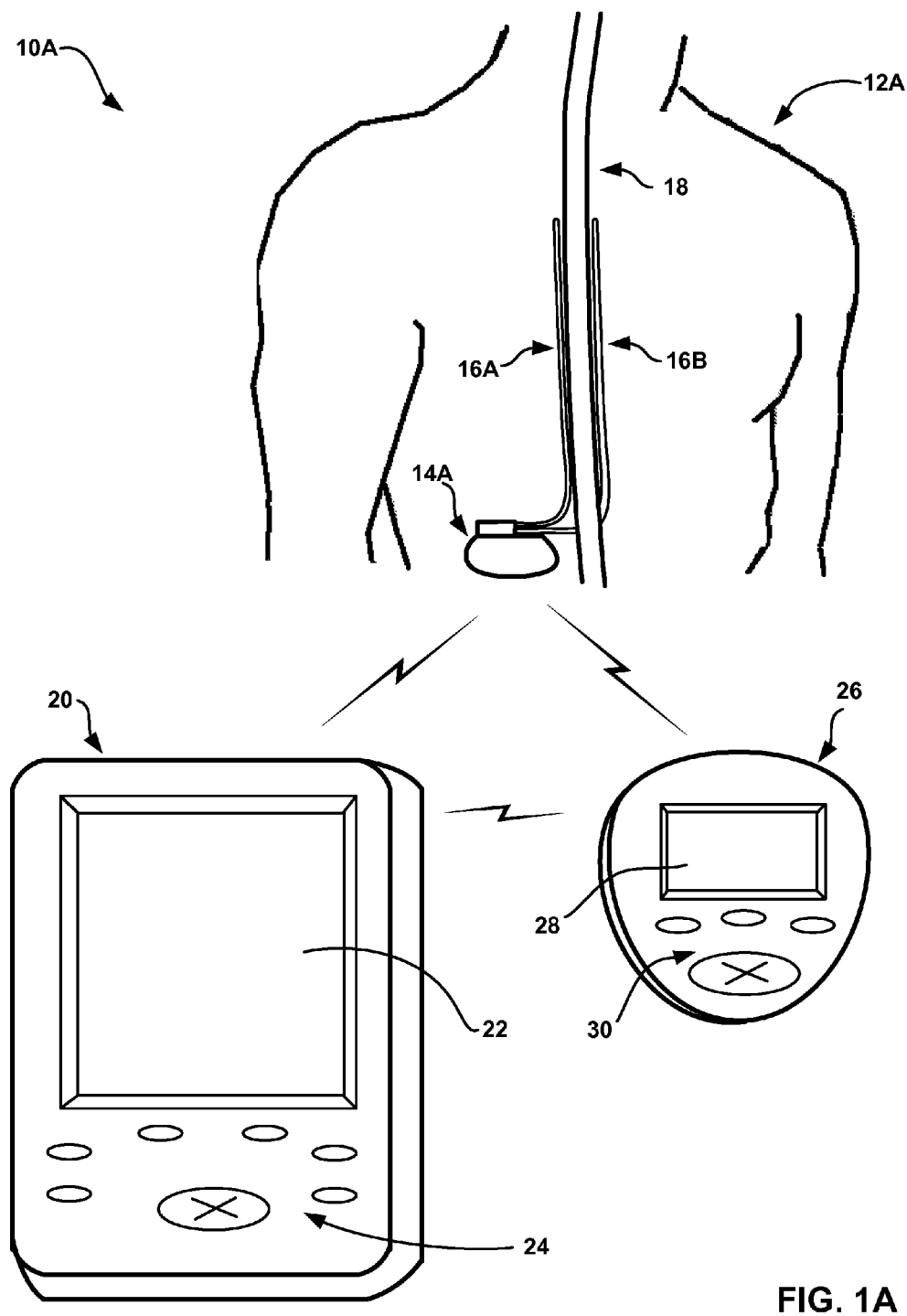
FIGS. 1A and 1B are conceptual diagrams illustrating example systems that include an implantable medical device that controls delivery of therapy based on a sensitivity analysis of a performance metric.
Figure 1B:
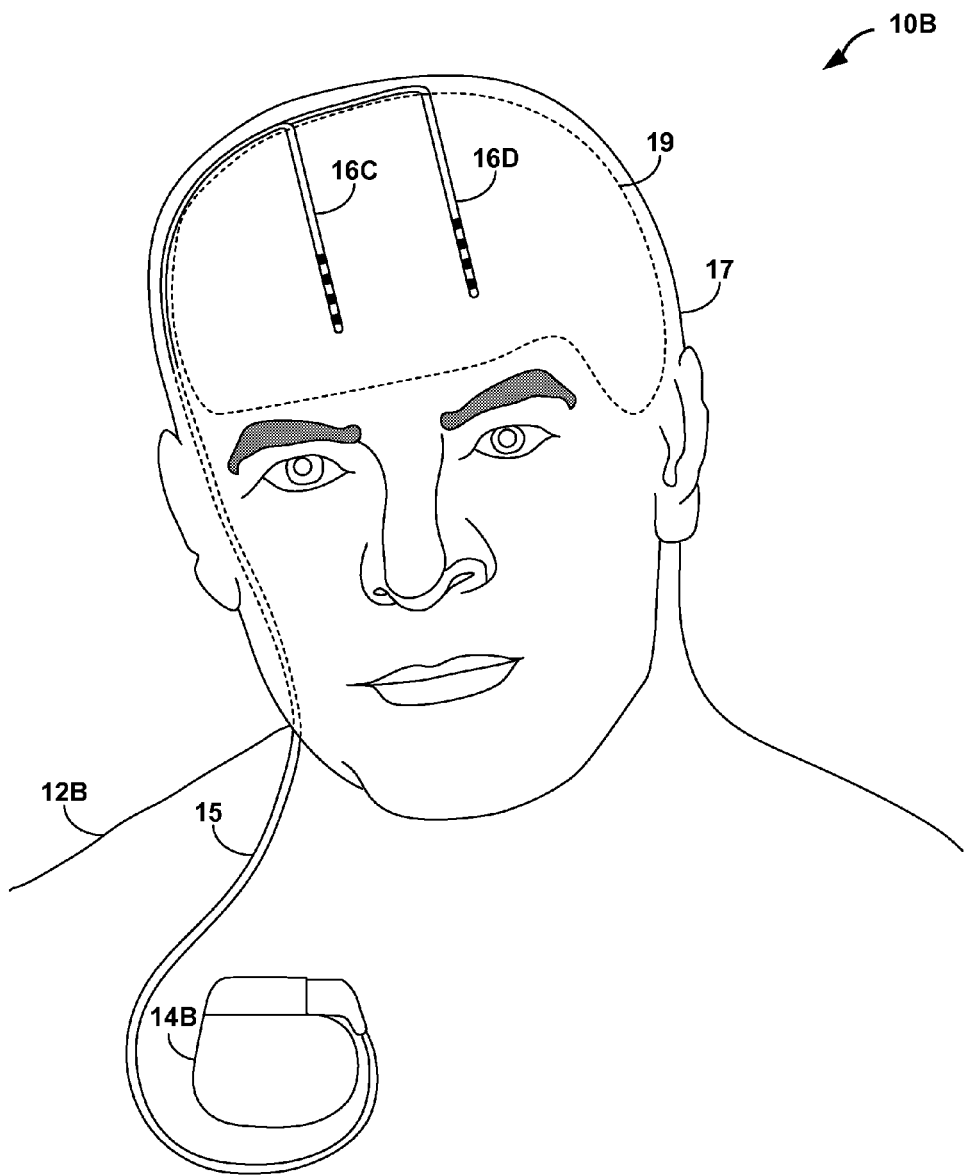

FIGS. 1A and 1B are conceptual diagrams illustrating example systems 10A and 10B (collectively "systems 10") that respectively include an implantable medical device (IMD) 14A or 14B (collectively "IMDs 14") controls delivery of a therapy to a respective one of patient 12A and 12B (collectively "patients 12") based on a sensitivity analysis of a performance metric. The performance metric may relate to efficacy or side effects. For example, the performance metric may comprise a sleep quality metric, a physical activity level metric, a posture metric, a movement disorder metric for patients with Parkinson's disease, tremor, spasticity, or multiple sclerosis, or the like. The sensitivity analysis determines values of a therapy parameter set that define a substantially maximum or minimum value of the performance metric. In particular, as will be described in greater detail below, IMDs 14 or another device may conduct the sensitivity analysis of the performance metric, and determine a baseline therapy parameter set based on the sensitivity analysis. IMDs 14 may control delivery of the therapy based on the baseline therapy parameter set. Furthermore, IMDs 14 or another device may periodically perturb at least one therapy parameter value of the baseline therapy parameter set to determine whether the performance metric value has changed over time.

Feedback entered by a patient 12, such as comments and/or a pain level value, may also be used as a performance metric to determine the baseline therapy parameter set. In some cases, a clinician or physician may determine a weighting scheme to provide more or less significance to the patient's feedback, i.e., the physician may choose to give the patient feedback zero weight and instead rely completely on other performance metric values, or the physician may judge that the patient has enough perspective to be able to competently gage pain levels and input substantially objective feedback into the sensitivity analysis.

Although the invention may use any performance metric, for purposes of illustration, the invention will be described herein as using a sleep quality metric to control the delivery of therapy to a patient. IMDs 14 may be able to adjust the therapy to address symptoms causing disturbed sleep, or symptoms that are worsened by disturbed sleep. In some embodiments, IMDs 14 delivers a therapy to treat chronic pain, which may both negatively impact the quality of sleep experienced by a patient 12, and be worsened by inadequate sleep quality. However, in other embodiments, IMDs 14 deliver therapy to treat movement disorders or psychological disorders, which similarly affect the patient.

In the illustrated example systems 10, IMDs 14 takes the form of an implantable neurostimulator that delivers neurostimulation therapy in the form of electrical pulses to patients 12. IMDs 14A and 14B deliver neurostimulation therapy to patients 12A and 12B via leads 16A and 16B, and leads 16C and 16D (collectively "leads 16"), respectively. Leads 16A and 16B may, as shown in FIG. 1A, be implanted proximate to the spinal cord 18 of patient 12A, and IMD 14A may deliver spinal cord stimulation (SCS) therapy to patient 12A in order to, for example, reduce pain experienced by patient 12A. However, the invention is not limited to the configuration of leads 16A and 16B shown in FIG. 1A, or to the delivery of SCS therapy.

For example, in another embodiment, illustrated in FIG. 1B, leads 16C and 16D may extend to brain 19 of patient 12B, e.g., through cranium 17 of patient. IMD 14B may deliver deep brain stimulation (DBS) or cortical stimulation therapy to patient 12 to treat any of a variety of non-respiratory neurological disorders, such as movement disorders or psychological disorders. Example therapies may treat tremor, Parkinson's disease, spasticity, epilepsy, depression or obsessive-compulsive disorder. As illustrated in FIG. 1B, leads 16C and 16D may be coupled to IMD 14B via one or more lead extensions 15.

As further examples, one or more leads 16 may be implanted proximate to the pelvic nerves (not shown) or stomach (not shown), and an IMD 14 may deliver neurostimulation therapy to treat incontinence or gastroparesis. Additionally, leads 16 may be implanted on or within the heart to treat any of a variety of cardiac disorders, such as congestive heart failure or arrhythmia, or may be implanted proximate to any peripheral nerves to treat any of a variety of disorders, such as peripheral neuropathy or other types of chronic pain.

The illustrated numbers and locations of leads 16 are merely examples. Embodiments of the invention may include any number of lead implanted at any of a variety of locations within a patient. Furthermore, the illustrated number and location of IMDs 14 are merely examples. IMDs 14 may be located anywhere within patient according to various embodiments of the invention. For example, in some embodiments, an IMD 14 may be implanted on or within cranium 17 for delivery of therapy to brain 19, or other structure of the head of the patient 12.

Moreover, the invention is not limited to implementation via an implantable neurostimulator, or even implementation via an IMD. In other words, any implantable or external medical device that delivers a therapy may control delivery of the therapy based on performance metric information, such as sleep quality information, according to the invention.

Further, the invention is not limited embodiments in which the therapy delivering medical device performs the sensitivity analysis. For example, in some embodiments, a computing device, such as a programming device, controls testing of therapy parameter sets by a therapy delivering medical device, receives performance metric values from the medical device, performs the sensitivity analysis, and provides a baseline therapy parameter set to the therapy delivering medical device. In some embodiments, multiple computing devices may cooperate to perform these functions. For example, a programming device may control testing of therapy parameter sets by the therapy delivering medical device and receive performance metric values from the medical device, while another computing device performs the sensitivity analysis on the performance metric values, and identifies the baseline therapy parameter set. The other computing device may provide the baseline therapy parameter set to the programming device, which may in turn provide the baseline therapy parameter set to the medical device. The other computing device may have a greater computing capacity than the programming device, which may allow it to more easily perform the sensitivity analysis, and may, for example, be a server coupled to the programming device by a network, such as a local area network (LAN), wide area network (WAN), or the Internet.

As another example, in some embodiments, the programming device or other computing device may receive values for one or more physiological parameters from the medical device, and may determine values for the performance metric based on the physiological parameter values. Further, in some embodiments of the invention, an implantable or external monitor separate from the therapy delivering medical device may monitor physiological parameters of the patient instead of, or in addition to the therapy delivering medical device. The monitor may determine values of the performance metric based on values of the physiological parameters, or transmit the physiological parameter values to a programming device or other computing device that determines the values of the performance metric. In some embodiments, the programming device and the monitor may be embodied within a single device.

Additionally, in some embodiments, a therapy device other than an IMD 14 may deliver therapy during the process of determining the baseline therapy parameter sets. The other therapy device may be an external or implantable trailing device, such as a trial neurostimulator or trial pump. The other therapy delivery device may monitor physiological parameter values of a patient 12, determine performance metric values, and perform the sensitivity analysis, as described herein with reference to an IMD 14. In other embodiments, some or all of these functions may be performed by a monitor, programming device, or other computing device, as described above. In such embodiments, an IMD 14 may deliver therapy according to a baseline therapy parameter set determined by a sensitivity analysis during a trialing period, and may perturb the therapy parameters for continued refinement of the baseline therapy parameter set, as will be described in greater detail below In the illustrated embodiment, an IMD 14 delivers therapy according to a set of therapy parameters, i.e., a set of values for a number of parameters that define the therapy delivered according to that therapy parameter set. In embodiments where an IMD 14 delivers neurostimulation therapy in the form of electrical pulses, the parameters may include voltage or current pulse amplitudes, pulse widths, pulse rates, duty cycles, durations, and the like. Further, each of leads 16 includes electrodes (not shown in FIGS. 1A and 1B), and a therapy parameter set may include information identifying which electrodes have been selected for delivery of pulses, and the polarities of the selected electrodes. In embodiments in which IMDs 14 deliver other types of therapies, therapy parameter sets may include other therapy parameters such as drug concentration and drug flow rate in the case of drug delivery therapy. Therapy parameter sets used by an IMD 14 may include a number of parameter sets programmed by a clinician (not shown), and parameter sets representing adjustments made by a patient 12 to these preprogrammed sets.

In other non-neurostimulator embodiments of the invention, an IMD 14 may still deliver therapy according to a different type of therapy parameter set. For example, implantable pump IMD embodiments may deliver a therapeutic agent to a patient according to a therapy parameter set that includes, for example, a dosage, an infusion rate, and/or a duty cycle.

Each of systems 10 may also include a clinician programmer 20 (illustrated as part of system 10A in FIG. 1A), which is an example of a programming device that may determine values of a performance metric and/or perform a sensitivity analysis, as described above. A clinician (not shown) may use clinician programmer 20 to program therapy for patient 12A, e.g., specify a number of therapy parameter sets and provide the parameter sets to IMD 14A. The clinician may also use clinician programmer 20 to retrieve information collected by IMD 14A. The clinician may use clinician programmer 20 to communicate with IMD 14A both during initial programming of IMD 14A, and for collection of information and further programming during follow-up visits.

Clinician programmer 20 may, as shown in FIG. 1A, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus, mouse, or the like. Keypad 24 may take the form of an alphanumeric keypad or a reduced set of keys associated with particular functions.

Systems 10 also include a patient programmer 26 (illustrated as part of system 10A in FIG. 1A), which also may, as shown in FIG. 1A, be a handheld computing device. Patient 12A may use patient programmer 26 to control the delivery of therapy by IMD 14A. For example, using patient programmer 26, patient 12A may select a current therapy parameter set from among the therapy parameter sets preprogrammed by the clinician, or may adjust one or more parameters of a preprogrammed therapy parameter set to arrive at the current therapy parameter set. As an example, patient 12A may increase or decrease pulse amplitude using patient programmer 26. Patient programmer 26 is also an example of a programming device that may determine values of a performance metric and/or perform a sensitivity analysis, as described above.

Patient programmer 26 may also include a display 28 and a keypad 30 to allow a patient 12 to interact with patient programmer 26. In some embodiments, display 26 may be a touch screen display, and a patient 12 may interact with patient programmer 26 via display 28. A patient 12 may also interact with patient programmer 26 using peripheral pointing devices, such as a stylus, mouse, or the like.

However, clinician and patient programmers 20, 26 are not limited to the hand-held computer embodiments illustrated in FIG. 1A. Programmers 20, 26 according to the invention may be any sort of computing device. For example, a programmer 20, 26 according to the invention may a tablet-based computing device, a desktop computing device, or a workstation.

An IMD 14, clinician programmer 20 and patient programmer 26 may, as shown in FIG. 1A, communicate via wireless communication. Clinician programmer 20 and patient programmer 26 may, for example, communicate via wireless communication with an IMD 14 using radio frequency (RF) or infrared telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of an IMD 14 and patient programmer 26 via remote telemetry techniques known in the art, communicating via a local area network (LAN), wide area network (WAN), public switched telephone network (PSTN), or cellular telephone network, for example.

As mentioned above, an IMD 14 controls delivery of a therapy, e.g., neurostimulation, to a patient 12 based on a sensitivity analysis of the sleep quality experienced by the patient. In some embodiments, as will be described in greater detail below, an IMD 14 conducts the sensitivity analysis to determine values of a therapy parameter set that defines a substantially maximum value of a sleep quality metric that indicates the quality of sleep experienced by a patient 12. An IMD 14 determines a baseline therapy parameter set based on the sensitivity analysis and controls delivery of the therapy to a patient 12, e.g., adjusts the therapy, based on the baseline therapy parameter set. Furthermore, an IMD 14 may periodically perturb at least one therapy parameter value of the baseline therapy parameter set to determine whether the sleep quality metric value has changed over time. The perturbation may occur at a preset time, in response to a change in a physiological parameter of a patient, or in response to a signal from a patient or a clinician. The therapy parameter values may be increased or decreased in small increments relative the therapy parameter range.

In some embodiments, an IMD 14 compares the sleep quality metric value defined by the baseline therapy parameter set to a sleep quality metric value defined by the perturbed therapy parameter values. An IMD 14 then adjusts the therapy delivered to a patient 12 based on the comparison. For example, an IMD 14 may maintain the baseline therapy parameter set when the comparison shows no improvement in the value of the sleep quality metric during perturbation. When the comparison shows improvement in the sleep quality metric value during perturbation, an IMD 14 updates the baseline therapy parameter set based on the one or more perturbed therapy parameter values.

In other embodiments, an implantable or external programmer, such as programmers 20 and 26, may perturb at least one therapy parameter value of the baseline therapy parameter set and an implantable or external monitoring device may monitor the sleep quality metric value. The programmer may also conduct the comparison and update the baseline parameter set based on the comparison. An implantable or external therapy device, such as an IMD 14, may then alter the therapy provided to the patient based on the updated baseline parameter set.

An IMD 14 may monitor one or more physiological parameters of the patient in order to determine values for one or more sleep quality metrics. Example physiological parameters that an IMD 14 may monitor include activity level, posture, heart rate, ECG morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, and eye motion. Some external medical device embodiments of the invention may additionally or alternatively monitor galvanic skin response. Further, in some embodiments, an IMD 14 additionally or alternatively monitors the variability of one or more of these parameters. In order to monitor one or more of these parameters, an IMD 14 may include, be coupled to, or be in wireless communication with one or more sensors (not shown in FIG. 1A), each of which outputs a signal as a function of one or more of these physiological parameters.

For example, an IMD 14 may determine sleep efficiency and/or sleep latency values. Sleep efficiency and sleep latency are example sleep quality metrics. An IMD 14 may measure sleep efficiency as the percentage of time while a patient 12 is attempting to sleep that the patient 12 is actually asleep. An IMD 14 may measure sleep latency as the amount of time between a first time when a patient 12 begins attempting to sleep and a second time when the patient 12 falls asleep, e.g., as an indication of how long it takes the patient 12 to fall asleep.

An IMD 14 may identify the time at which patient begins attempting to fall asleep in a variety of ways. For example, an IMD 14 may receive an indication from the patient that the patient is trying to fall asleep via patient programmer 26. In other embodiments, an IMD 14 may monitor the activity level of a patient 12, and identify the time when the patient 12 is attempting to fall asleep by determining whether the patient 12 has remained inactive for a threshold period of time, and identifying the time at which the patient 12 became inactive. In still other embodiments, an IMD 14 may monitor the posture of a patient 12, and may identify the time when the patient 12 becomes recumbent, e.g., lies down, as the time when the patient 12 is attempting to fall asleep. In these embodiments, an IMD 14 may also monitor the activity level of a patient 12, and confirm that the patient 12 is attempting to sleep based on the activity level.

An IMD 14 may identify the time at which a patient 12 has fallen asleep based on the activity level of the patient and/or one or more of the other physiological parameters that may be monitored by the IMD 14 as indicated above. For example, an IMD 14 may identify a discernable change, e.g., a decrease, in one or more physiological parameters, or the variability of one or more physiological parameters, which may indicate that a patient 12 has fallen asleep. In some embodiments, an IMD 14 determines a sleep probability metric value based on a value of a physiological parameter monitored by the medical device. In such embodiments, the sleep probability metric value may be compared to a threshold to identify when the patient has fallen asleep. In some embodiments, a sleep probability metric value is determined based on a value of each of a plurality of physiological parameters, the sleep probability values are averaged or otherwise combined to provide an overall sleep probability metric value, and the overall sleep probability metric value is compared to a threshold to identify the time that the patient falls asleep.

Other sleep quality metrics include total time sleeping per day, and the amount or percentage of time sleeping during nighttime or daytime hours per day. In some embodiments, an IMD 14 may be able to detect arousal events and apneas occurring during sleep based on one or more monitored physiological parameters, and the number of apnea and/or arousal events per night may be determined as a sleep quality metric. Further, in some embodiments, an IMD 14 may be able to determine which sleep state a patient 12 is in based on one or more monitored physiological parameters, e.g., rapid eye movement (REM), S1, S2, S3, or S4, and the amount of time per day spent in these various sleep states may be a sleep quality metric.

Figure 2A:
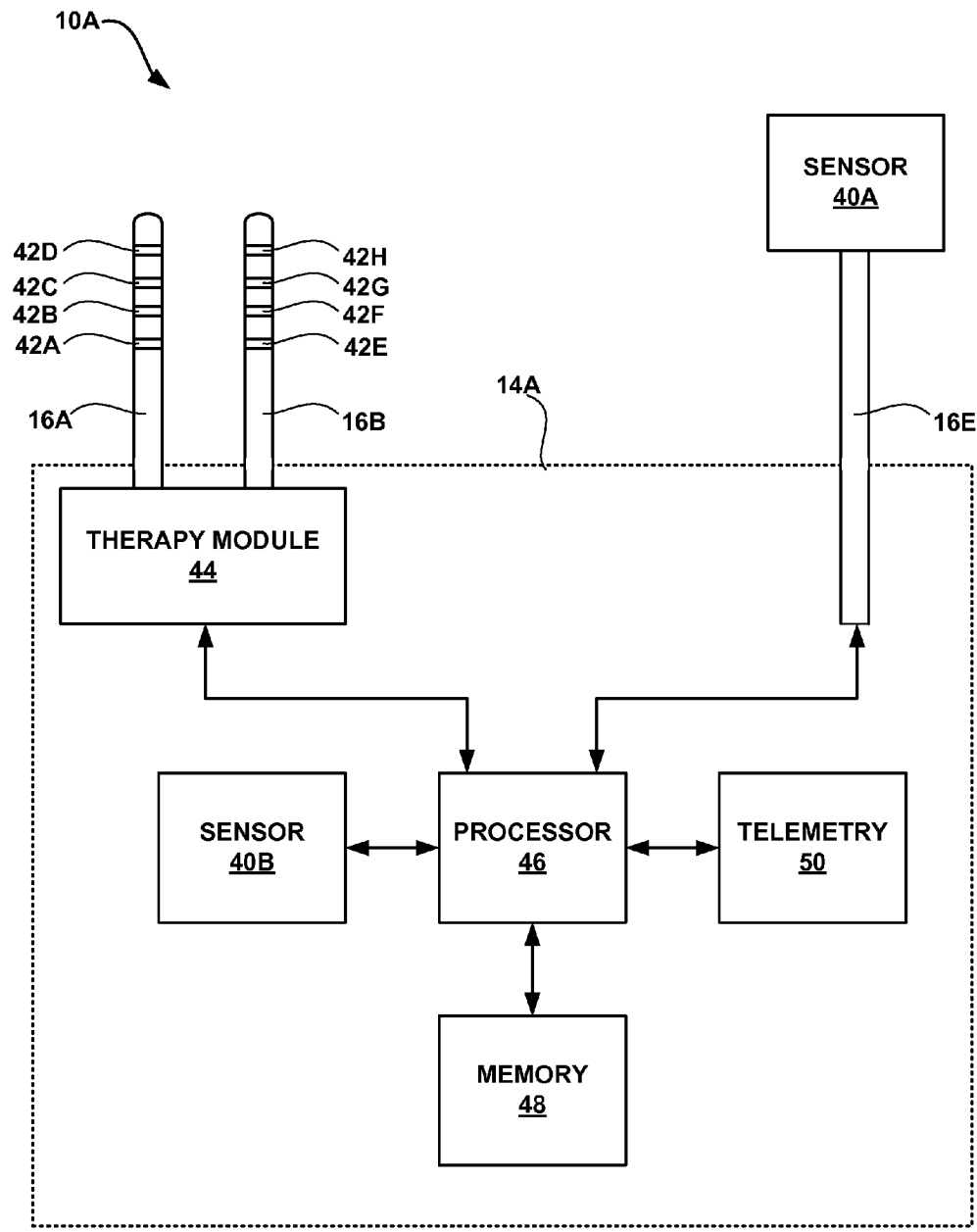
FIGS. 2A and 2B are block diagrams further illustrating the example systems and implantable medical devices of FIGS. 1A and 1B.
Figure 2B:
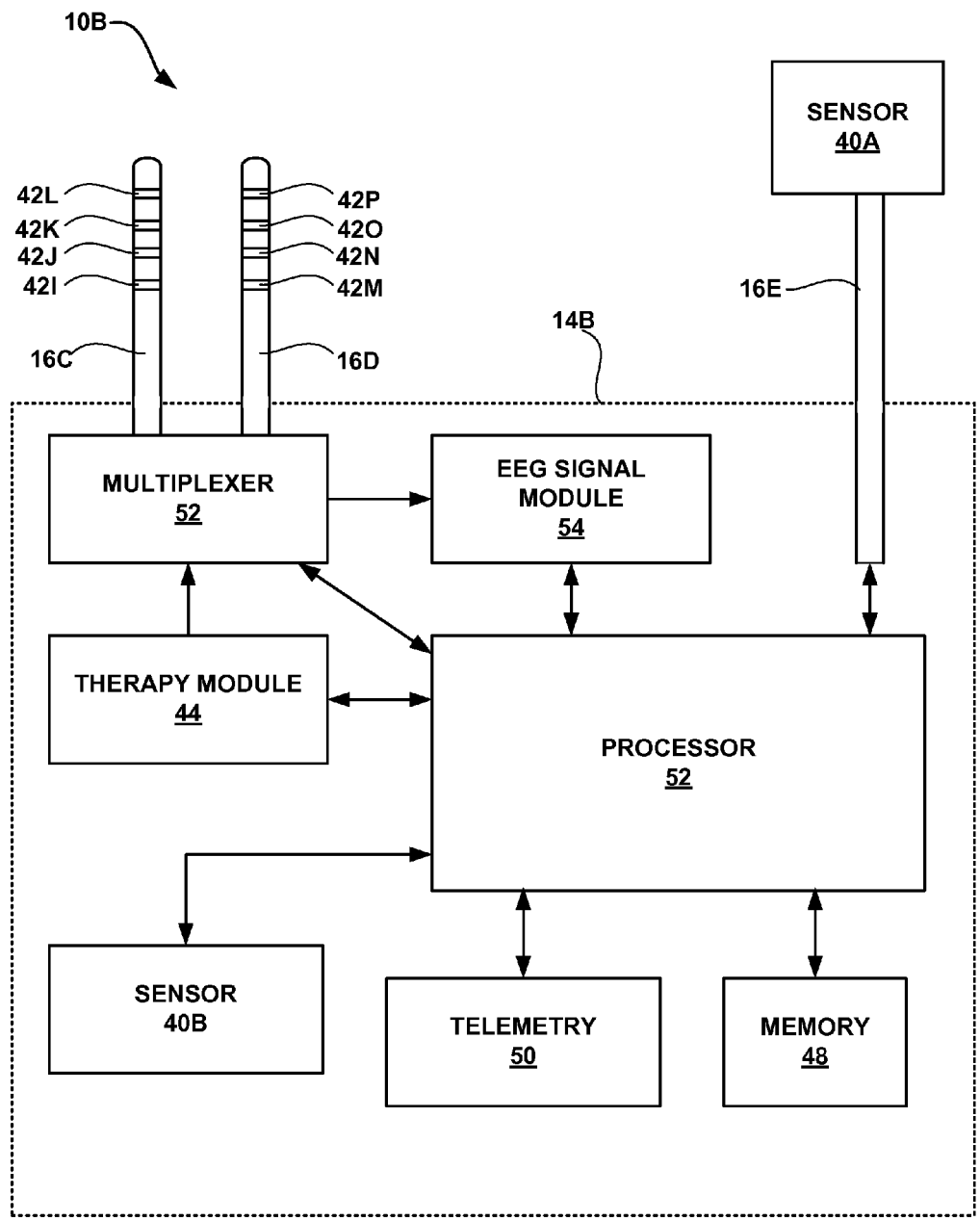

FIGS. 2A and 2B are block diagrams further illustrating systems 10A and 10B. In particular, FIG. 2A illustrates an example configuration of IMD 14A and leads 16A and 16B. FIG. 2B illustrates an example configuration of IMD 14B and leads 16C and 16D. FIGS. 2A and 2B also illustrate sensors 40A and 40B (collectively "sensors 40") that output signals as a function of one or more physiological parameters of a patient 12.

IMD 14A may deliver neurostimulation therapy via electrodes 42A-D of lead 16A and electrodes 42E-H of lead 16B, while IMD 14B delivers neurostimulation via electrodes 42I-L of lead 16C and electrodes 42 M-P of lead 16D (collectively "electrodes 42"). Electrodes 42 may be ring electrodes. The configuration, type and number of electrodes 42 illustrated in FIGS. 2A and 2B are merely exemplary. For example, leads 16 may each include eight electrodes 42, and the electrodes 42 need not be arranged linearly on each of leads 16.

In each of systems 10A and 10B, electrodes 42 are electrically coupled to a therapy delivery module 44 via leads 16. Therapy delivery module 44 may, for example, include an output pulse generator coupled to a power source such as a battery. Therapy delivery module 44 may deliver electrical pulses to a patient 12 via at least some of electrodes 42 under the control of a processor 46, which controls therapy delivery module 44 to deliver neurostimulation therapy according to one or more neurostimulation therapy programs selected from available programs stored in a memory 48. However, the invention is not limited to implantable neurostimulator embodiments or even to IMDs that deliver electrical stimulation. For example, in some embodiments, a therapy delivery module of an IMD may include a pump, circuitry to control the pump, and a reservoir to store a therapeutic agent for delivery via the pump, and a processor of the IMD may control delivery of a therapeutic agent by the pump according to an infusion program selected from among a plurality of infusion programs stored in a memory.

An IMD 14 may also include a telemetry circuit 50 that enables processor 46 to communicate with programmers 20, 26. Via telemetry circuit 50, processor 46 may receive therapy programs specified by a clinician from clinician programmer 20 for storage in memory 48. Processor 46 may also receive program selections and therapy adjustments made by a patient 12 using patient programmer 26 via telemetry circuit 50. In some embodiments, processor 46 may provide diagnostic information recorded by processor 46 and stored in memory 48 to one of programmers 20, 26 via telemetry circuit 50.

Processor 46 may include a microprocessor, a controller, a digital signal processor (DSP), an application specific integrated circuit (ASIC), a field-programmable gate array (FPGA), discrete logic circuitry, or the like. Memory 48 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 48 stores program instructions that, when executed by processor 46, cause IMD 14 and processor 46 to perform the functions attributed to them herein.

Each of sensors 40 outputs a signal as a function of one or more physiological parameters of a patient 12. An IMD 14 may include circuitry (not shown) that conditions the signals output by sensors 40 such that they may be analyzed by processor 46. For example, an IMD 14 may include one or more analog to digital converters to convert analog signals output by sensors 40 into digital signals usable by processor 46, as well as suitable filter and amplifier circuitry. Although shown as including two sensors 40, systems 10 may include any number of sensors.

Further, as illustrated in FIGS. 2A and 2B, sensors 40 may be included as part of IMDs 14, or coupled to IMDs 14 via leads 16. Sensors 40 may be coupled to IMDs 14 via therapy leads 16A-16D, or via other leads 16, such as lead 16E depicted in FIGS. 2A and 2B. In some embodiments, a sensor located outside of an IMD 14 may be in wireless communication with processor 46. Wireless communication between sensors 40 and IMDs 14 may, as examples, include RF communication or communication via electrical signals conducted through the tissue and/or fluid of a patient 12.

As discussed above, exemplary physiological parameters of a patient 12 that may be monitored by an IMD 14 to determine values of one or more sleep quality metrics include activity level, posture, heart rate, ECG morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, and eye motion. Further, as discussed above, external medical device embodiments of the invention may additionally or alternatively monitor galvanic skin response. Sensors 40 may be of any type known in the art capable of outputting a signal as a function of one or more of these parameters.

In some embodiments, in order to determine one or more sleep quality metric values, processor 46 determines when a patient 12 is attempting to fall asleep. For example, processor 46 may identify the time that patient begins attempting to fall asleep based on an indication received from a patient 12, e.g., via clinician programmer 20 and a telemetry circuit 50. In other embodiments, processor 46 identifies the time that a patient 12 begins attempting to fall asleep based on the activity level of the patient 12.

In such embodiments, an IMD 14 may include one or more sensors 40 that generate a signal as a function of patient activity. For example, sensors 40 may include one or more accelerometers, gyros, mercury switches, or bonded piezoelectric crystals that generates a signal as a function of patient activity, e.g., body motion, footfalls or other impact events, and the like. Additionally or alternatively, sensors 40 may include one or more electrodes that generate an electromyogram (EMG) signal as a function of muscle electrical activity, which may indicate the activity level of a patient. The electrodes may be, for example, located in the legs, abdomen, chest, back or buttocks of a patient 12 to detect muscle activity associated with walking, running, or the like. The electrodes may be coupled to an IMD 14 by leads 16 or wirelessly, or, if the IMD 14 is implanted in these locations, integrated with a housing of the IMD 14.

However, bonded piezoelectric crystals located in these areas generate signals as a function of muscle contraction in addition to body motion, footfalls or other impact events. Consequently, use of bonded piezoelectric crystals to detect activity of a patient 12 may be preferred in some embodiments in which it is desired to detect muscle activity in addition to body motion, footfalls, or other impact events. Bonded piezoelectric crystals may be coupled to an IMD 14 via leads 16 or wirelessly, or piezoelectric crystals may be bonded to the can of the IMD 14 when the IMD is implanted in these areas, e.g., in the back, chest, buttocks or abdomen of a patient 12.

Processor 46 may identify a time when the activity level of a patient 12 falls below a threshold activity level value stored in memory 48, and may determine whether the activity level remains substantially below the threshold activity level value for a threshold amount of time stored in memory 48. In other words, a patient 12 remaining inactive for a sufficient period of time may indicate that the patient 12 is attempting to fall asleep. If processor 46 determines that the threshold amount of time is exceeded, processor 46 may identify the time at which the activity level fell below the threshold activity level value as the time that a patient 12 began attempting to fall asleep.

In some embodiments, processor 46 determines whether a patient 12 is attempting to fall asleep based on whether the patient 12 is or is not recumbent, e.g., lying down. In such embodiments, sensors 40 may include a plurality of accelerometers, gyros, or magnetometers oriented orthogonally that generate signals which indicate the posture of a patient 12. In addition to being oriented orthogonally with respect to each other, each of sensors 40 used to detect the posture of a patient 12 may be generally aligned with an axis of the body of the patient 12. In exemplary embodiments, an IMD 14 includes three orthogonally oriented posture sensors 40.

When sensors 40 include accelerometers, for example, that are aligned in this manner, processor 46 may monitor the magnitude and polarity of DC components of the signals generated by the accelerometers to determine the orientation of a patient 12 relative to the Earth's gravity, e.g., the posture of a patient 12. In particular, the processor 46 may compare the DC components of the signals to respective threshold values stored in memory 48 to determine whether a patient 12 is or is not recumbent. Further information regarding use of orthogonally aligned accelerometers to determine patient posture may be found in a commonly assigned U.S. Pat. No. 5,593,431, which issued to Todd J. Sheldon.

Other sensors 40 that may generate a signal that indicates the posture of a patient 12 include electrodes that generate an electromyogram (EMG) signal, or bonded piezoelectric crystals that generate a signal as a function of contraction of muscles. Such sensors 40 may be implanted in the legs, buttocks, abdomen, or back of a patient 12, as described above. The signals generated by such sensors when implanted in these locations may vary based on the posture of a patient 12, e.g., may vary based on whether the patient is standing, sitting, or laying down.

Further, the posture of a patient 12 may affect the thoracic impedance of the patient. Consequently, sensors 40 may include an electrode pair, such as one electrode integrated with the housing of an IMD 14 and one of electrodes 42, that generates a signal as a function of the thoracic impedance of the patient 12, and processor 46 may detect the posture or posture changes of patient the 12 based on the signal. The electrodes of the pair may be located on opposite sides of the patient's thorax. For example, the electrode pair may include one of electrodes 42 located proximate to the spine of a patient for delivery of SCS therapy, and an IMD 14 with an electrode integrated in its housing may be implanted in the abdomen of a patient 12.

Additionally, changes of the posture of a patient 12 may cause pressure changes with the cerebrospinal fluid (CSF) of the patient. Consequently, sensors 40 may include pressure sensors coupled to one or more intrathecal or intracerebroventricular catheters, or pressure sensors coupled to IMD 14 wirelessly or via lead 16. CSF pressure changes associated with posture changes may be particularly evident within the brain of the patient, e.g., may be particularly apparent in an intracranial pressure (ICP) waveform.

In some embodiments, processor 46 considers both the posture and the activity level of a patient 12 when determining whether the patient 12 is attempting to fall asleep. For example, processor 46 may determine whether a patient 12 is attempting to fall asleep based on a sufficiently long period of sub-threshold activity, as described above, and may identify the time that patient began attempting to fall asleep as the time when the patient 12 became recumbent. Any of a variety of combinations or variations of these techniques may be used to determine when a patient 12 is attempting to fall asleep, and a specific one or more techniques may be selected based on the sleeping and activity habits of a particular patient.

Processor 46 may also determine when a patient 12 is asleep, e.g., identify the times that the patient 12 falls asleep and wakes up, in order to determine one or more sleep quality metric values. The detected values of physiological parameters of a patient 12, such as activity level, heart rate, values of ECG morphological features, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response may discernibly change when the patient 12 falls asleep or wakes up. In particular, these physiological parameters may be at low values when a patient 12 is asleep. Further, the variability of at least some of these parameters, such as heart rate and respiration rate, may be at a low value when the patient is asleep.

Consequently, in order to detect when a patient 12 falls asleep and wakes up, processor 46 may monitor one or more of these physiological parameters, or the variability of these physiological parameters, and detect the discernable changes in their values associated with a transition between a sleeping state and an awake state.

In some embodiments, in order to determine whether a patient 12 is asleep, processor 46 monitors a plurality of physiological parameters, and determines a value of a metric that indicates the probability that the patient 12 is asleep for each of the parameters based on a value of the parameter. In particular, the processor 46 may apply a function or look-up table to the current value, and/or the variability of each of a plurality of physiological parameters to determine a sleep probability metric value for each of the plurality of physiological parameters. A sleep probability metric value may be a numeric value, and in some embodiments may be a probability value, e.g., a number within the range from 0 to 1, or a percentage level.

Processor 46 may average or otherwise combine the plurality of sleep probability metric values to provide an overall sleep probability metric value. In some embodiments, processor 46 may apply a weighting factor to one or more of the sleep probability metric values prior to combination. Processor 46 may compare the overall sleep probability metric value to one or more threshold values stored in memory 48 to determine when a patient 12 falls asleep or awakes. Use of sleep probability metric values to determine when a patient is asleep based on a plurality of monitored physiological parameters is described in greater detail in a commonly assigned and copending U.S. patent application Ser. No. 11/691,405, by Ken Heruth and Keith Miesel, entitled "DETECTING SLEEP," filed on Mar. 26, 2007, which is incorporated herein by reference in its entirety.

To enable processor 46 to determine when a patient 12 is asleep or awake, sensors 40 may include, for example, activity sensors as described above. In some embodiments, the activity sensors may include electrodes or bonded piezoelectric crystals, which may be implanted in the back, buttocks, chest, or abdomen of a patient 12 as described above. In such embodiments, processor 46 may detect the electrical activation and contractions of muscles associated with gross motor activity of the patient, e.g., walking, running or the like via the signals generated by such sensors. Processor 46 may also detect spasmodic or pain related muscle activation via the signals generated by such sensors. Spasmodic or pain related muscle activation may indicate that a patient 12 is not sleeping, e.g., unable to sleep, or if the patient 12 is sleeping, may indicate a lower level of sleep quality.

As another example, sensors 40 may include electrodes located on leads or integrated as part of the housing of an IMD 14 that output an electrogram signal as a function of electrical activity of the heart of a patient 12, and processor 46 may monitor the heart rate of the patient 12 based on the electrogram signal. In other embodiments, a sensor may include an acoustic sensor within an IMD 14, a pressure sensor within the bloodstream or cerebrospinal fluid of a patient 12, or a temperature sensor located within the bloodstream of the patient 12. The signals output by such sensors may vary as a function of contraction of the heart of a patient 12, and can be used by an IMD 14 to monitor the heart rate of the patient 12.

In some embodiments, processor 46 may detect, and measure values for one or more ECG morphological features within an electrogram generated by electrodes as described above. ECG morphological features may vary in a manner that indicates whether a patient 12 is asleep or awake. For example, the amplitude of the ST segment of the ECG may decrease when a patient 12 is asleep. Further, the amplitude of QRS complex or T-wave may decrease, and the widths of the QRS complex and T-wave may increase when a patient 12 is asleep. The QT interval and the latency of an evoked response may increase when a patient 12 is asleep, and the amplitude of the evoked response may decrease when the patient 12 is asleep.

In some embodiments, sensors 40 may include an electrode pair, including one electrode integrated with the housing of an IMD 14 and one of electrodes 16, that output a signal as a function of the thoracic impedance of the patient 12 as described above, which varies as a function of respiration by the patient 12. In other embodiments, sensors 40 may include a strain gauge, bonded piezoelectric element, or pressure sensor within the blood or CSF that outputs a signal that varies based on patient respiration. An electrogram output by electrodes as discussed above may also be modulated by patient respiration, and may be used as an indirect representation of respiration rate.

Sensors 40 may include electrodes that output an electromyogram (EMG) signal as a function of muscle electrical activity, as described above, or may include any of a variety of known temperature sensors to output a signal as a function of a core or subcutaneous temperature of a patient 12. Such electrodes and temperature sensors may be incorporated within the housing of an IMD 14, or coupled to the IMD 14 wirelessly or via leads. Sensors 40 may also include a pressure sensor within, or in contact with, a blood vessel. The pressure sensor may output a signal as a function of the a blood pressure of a patient 12, and may, for example, comprise a Chronicle Hemodynamic Monitor™ commercially available from Medtronic, Inc. of Minneapolis, Minn. Further, certain muscles of a patient 12, such as the muscles of the patient's neck, may discernibly relax when the patient 12 is asleep or within certain sleep states. Consequently, sensors 40 may include strain gauges or EMG electrodes implanted in such locations that generate a signal as a function of muscle tone.

Sensors 40 may also include optical pulse oximetry sensors or Clark dissolved oxygen sensors located within, as part of a housing of, or outside of an IMD 14, which output signals as a function blood oxygen saturation and blood oxygen partial pressure respectively. In some embodiments, systems 10 may include a catheter with a distal portion located within the cerebrospinal fluid of a patient 12, and the distal end may include a Clark dissolved oxygen sensor to output a signal as a function of the partial pressure of oxygen within the cerebrospinal fluid. Embodiments in which an IMD comprises an implantable pump, for example, may include a catheter with a distal portion located in the cerebrospinal fluid.

In some embodiments, sensors 40 may include one or more intraluminal, extraluminal, or external flow sensors positioned to output a signal as a function of arterial blood flow. A flow sensor may be, for example, and electromagnetic, thermal convection, ultrasonic-Doppler, or laser-Doppler flow sensor. Further, in some external medical device embodiments of the invention, sensors 40 may include one or more electrodes positioned on the skin of a patient 12 to output a signal as a function of galvanic skin response.

Additionally, in some embodiments, sensors 40 may include one or more electrodes positioned within or proximate to the brain of patient, which detect electrical activity of the brain. For example, in embodiments in which an IMD 14 delivers stimulation or other therapy to the brain, processor 46 may be coupled to electrodes implanted on or within the brain via a lead 16. System 10B, illustrated in FIGS. 1B and 2B, is an example of a system that includes electrodes 42, located on or within the brain of patient 12B, that are coupled to IMD 14B.

As shown in FIG. 2B, electrodes 42 may be selectively coupled to therapy module 44 or an EEG signal module 54 by a multiplexer 52, which operates under the control of processor 46. EEG signal module 54 receives signals from a selected set of the electrodes 42 via multiplexer 52 as controlled by processor 46. EEG signal module 54 may analyze the EEG signal for certain features indicative of sleep or different sleep states, and provide indications of relating to sleep or sleep states to processor 46. Thus, electrodes 42 and EEG signal module 54 may be considered another sensor 40 in system 10B. IMD 14B may include circuitry (not shown) that conditions the EEG signal such that it may be analyzed by processor 52. For example, IMD 14B may include one or more analog to digital converters to convert analog signals received from electrodes 42 into digital signals usable by processor 46, as well as suitable filter and amplifier circuitry.

In some embodiments, processor 46 will only request EEG signal module 54 to operate when one or more other physiological parameters indicate that patient 12B is already asleep. However, processor 46 may also direct EEG signal module to analyze the EEG signal to determine whether patient 12B is sleeping, and such analysis may be considered alone or in combination with other physiological parameters to determine whether patient 12B is asleep. EEG signal module 60 may process the EEG signals to detect when patient 12 is asleep using any of a variety of techniques, such as techniques that identify whether a patient is asleep based on the amplitude and/or frequency of the EEG signals. In some embodiments, the functionality of EEG signal module 54 may be provided by processor 46, which, as described above, may include one or more microprocessors, ASICs, or the like.

In other embodiments, processor 46 may be wirelessly coupled to electrodes that detect brain electrical activity. For example, one or more modules may be implanted beneath the scalp of the patient, each module including a housing, one or more electrodes, and circuitry to wirelessly transmit the signals detected by the one or more electrodes to an IMD 14. In other embodiments, the electrodes may be applied to the patient's scalp, and electrically coupled to a module that includes circuitry for wirelessly transmitting the signals detected by the electrodes to an IMD 14. The electrodes may be glued to the scalp, or a headband, hair net, cap, or the like may incorporate the electrodes and the module, and may be worn by a patient 12 to apply the electrodes to the patient's scalp when, for example, the patient is attempting to sleep. The signals detected by the electrodes and transmitted to an IMD 14 may be electroencephalogram (EEG) signals, and processor 46 may process the EEG signals to detect when the patient 12 is asleep using any of a variety of known techniques, such as techniques that identify whether a patient is asleep based on the amplitude and/or frequency of the EEG signals.

Also, the motion of the eyes of a patient 12 may vary depending on whether the patient is sleeping and which sleep state the patient is in. Consequently, sensors 40 may include electrodes place proximate to the eyes of a patient 12 to detect electrical activity associated with motion of the eyes, e.g., to generate an electro-oculography (EOG) signal. Such electrodes may be coupled to an IMD 14 via one or more leads 16, or may be included within modules that include circuitry to wirelessly transmit detected signals to the IMD 14. Wirelessly coupled modules incorporating electrodes to detect eye motion may be worn externally by a patient 12, e.g., attached to the skin of the patient 12 proximate to the eyes by an adhesive when the patient is attempting to sleep.

Processor 46 may also detect arousals and/or apneas that occur when a patient 12 is asleep based on one or more of the above-identified physiological parameters. For example, processor 46 may detect an arousal based on an increase or sudden increase in one or more of heart rate, heart rate variability, respiration rate, respiration rate variability, blood pressure, or muscular activity as the occurrence of an arousal. Processor 46 may detect an apnea based on a disturbance in the respiration rate of a patient 12, e.g., a period with no respiration.

Processor 46 may also detect arousals or apneas based on sudden changes in one or more of the ECG morphological features identified above. For example, a sudden elevation of the ST segment within the ECG may indicate an arousal or an apnea. Further, sudden changes in the amplitude or frequency of an EEG signal, EOG signal, or muscle tone signal may indicate an apnea or arousal. Memory 48 may store thresholds used by processor 46 to detect arousals and apneas. Processor 46 may determine, as a sleep quality metric value, the number of apnea events and/or arousals during a night.

Further, in some embodiments, processor 46 may determine which sleep state a patient 12 is in during sleep, e.g., REM, S1, S2, S3, or S4, based on one or more of the monitored physiological parameters. In some embodiments, memory 48 may store one or more thresholds for each of sleep states, and processor 46 may compare physiological parameter or sleep probability metric values to the thresholds to determine which sleep state a patient 12 is currently in. Processor 46 may determine, as sleep quality metric values, the amounts of time per night spent in the various sleep states. Further, in some embodiments, processor 46 may use any of a variety of known techniques for determining which sleep state patient is in based on an EEG signal, which processor 46 may receive via electrodes as described above, such as techniques that identify sleep state based on the amplitude and/or frequency of the EEG signals. In some embodiments, processor 46 may also determine which sleep state patient is in based on an EOG signal, which processor 46 may receive via electrodes as described above, either alone or in combination with an EEG signal, using any of a variety of techniques known in the art. Inadequate time spent in deeper sleep states, e.g., S3 and S4, is an indicator of poor sleep quality.

Figure 3:
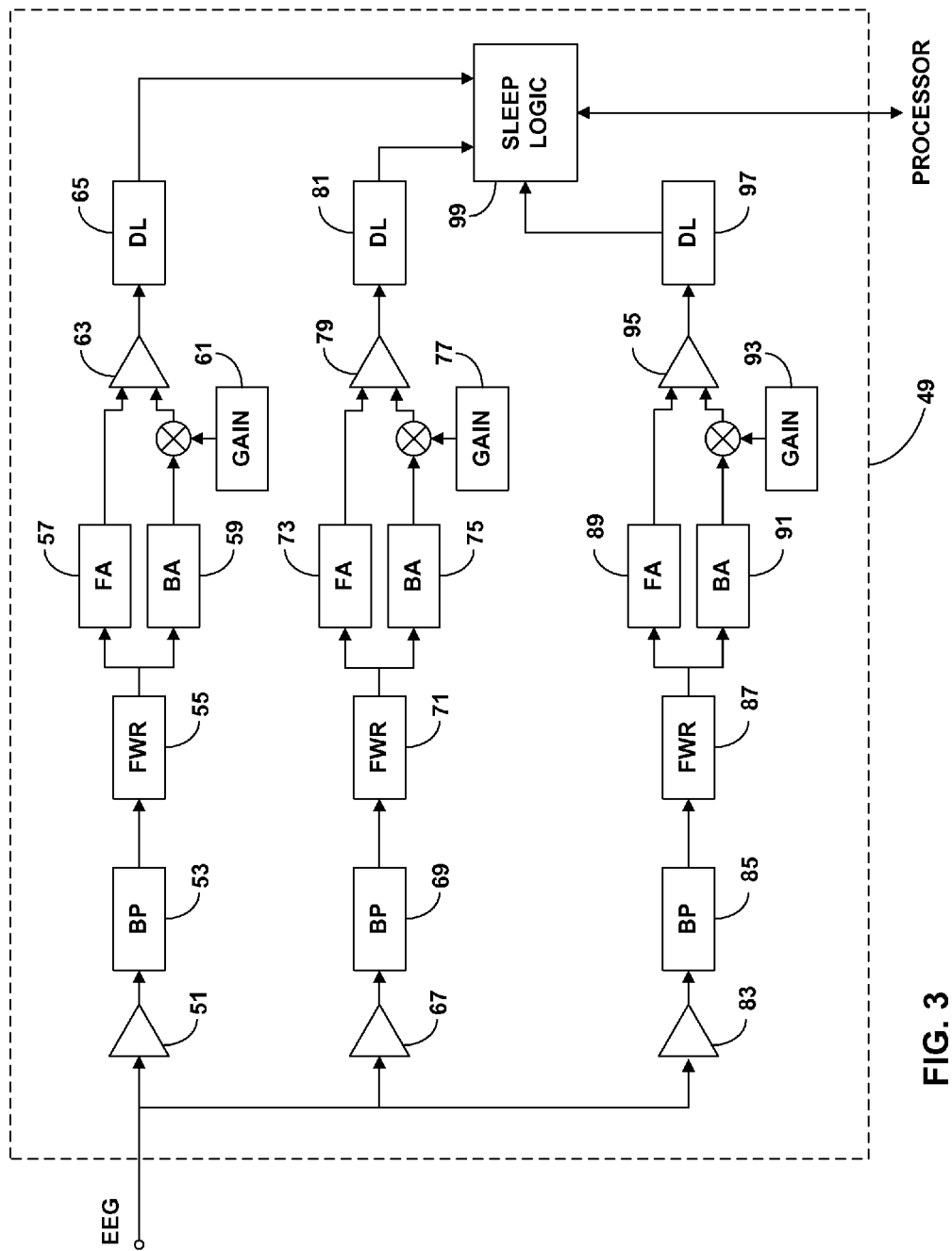
FIG. 3 is a logic diagram illustrating an example circuit that detects the sleep state of a patient from the electroencephalogram (EEG) signal.

FIG. 3 is a logical diagram of an example circuit that detects sleep or the sleep type of a patient based on the electroencephalogram (EEG) signal. Module 49, shown in FIG. 3, may be integrated into an EEG signal module 54 of IMD 14B, or some other implantable or external device capable of detecting an EEG signal according to other embodiments of the invention (e.g., IMD 14A). In such embodiments, module 49 may be used to, for example, determine whether a patient 12 is asleep, or in which sleep state the patient is.

An EEG signal detected by electrodes 42 adjacent to the brain 19 of patent 12B is transmitted into module 49 and provided to three channels, each of which includes a respective one of amplifiers 51, 67 and 83, and bandpass filters 53, 69 and 85. In other embodiments, a common amplifier amplifies the EEG signal prior to filters 53, 69 and 85. Bandpass filter 53 allows frequencies between approximately 4 Hz and approximately 8 Hz, and signals within the frequency range may be prevalent in the EEG during S1 and S2 sleep states. Bandpass filter 69 allows frequencies between approximately 1 Hz and approximately 3 Hz, which may be prevalent in the EEG during the S3 and S4 sleep states. Bandpass filter 85 allows frequencies between approximately 10 Hz and approximately 50 Hz, which may be prevalent in the EEG during REM sleep. Each resulting signal may then processed to identify in which sleep state patient 12B is.

After bandpass filtering of the original EEG signal, the filtered signals are similarly processed in parallel before being delivered to sleep logic module 99. For ease of discussion, only one of the three channels will be discussed herein, but each of the filtered signals may be processed similarly. Once the EEG signal is filtered by bandpass filter 53, the signal is rectified by full-wave rectifier 55. Modules 57 and 59 respectively determine the foreground average and background average so that the current energy level can be compared to a background level at comparator 63. The signal from background average is increased by gain 61 before being sent to comparator 63, because comparator 63 operates in the range of millivolts or volts while the EEG signal amplitude is originally on the order of microvolts. The signal from comparator 63 is indicative of sleep stages S1 and S2. If duration logic 65 determines that the signal is greater than a predetermined level for a predetermined amount of time, the signal is sent to sleep logic module 99 indicating that patient 12 may be within the S1 or S2 sleep states. In some embodiments, as least duration logic 65, 81, 97 and sleep logic 99 may be embodied in a processor of the device containing EEG module 49.

Module 49 may detect all sleep types for patient 12. Further, the beginning of sleep may be detected by module 49 based on the sleep state of patient 12. Some of the components of module 49 may vary from the example of FIG. 3. For example, gains 61, 77 and 93 may be provided from the same power source. Module 49 may be embodied as analog circuitry, digital circuitry, or a combination thereof.

In other embodiments, module 49 may not need to reference the background average to determine the current state of sleep of patient 12. Instead, the power of the signals from bandpass filters 53, 69 and 85 are compared to each other, and sleep logic module 99 determines which the sleep state of patient 12 based upon the frequency band that has the highest power. In this case, the signals from full-wave rectifiers 55, 71 and 87 are sent directly to a device that calculates the signal power, such as a spectral power distribution module (SPD), and then to sleep logic module 99 which determines the frequency band of the greatest power, e.g., the sleep state of patient 12B. In some cases, the signal from full-wave rectifiers 55, 71 and 87 may be normalized by a gain component to correctly weight each frequency band.

Figure 4:
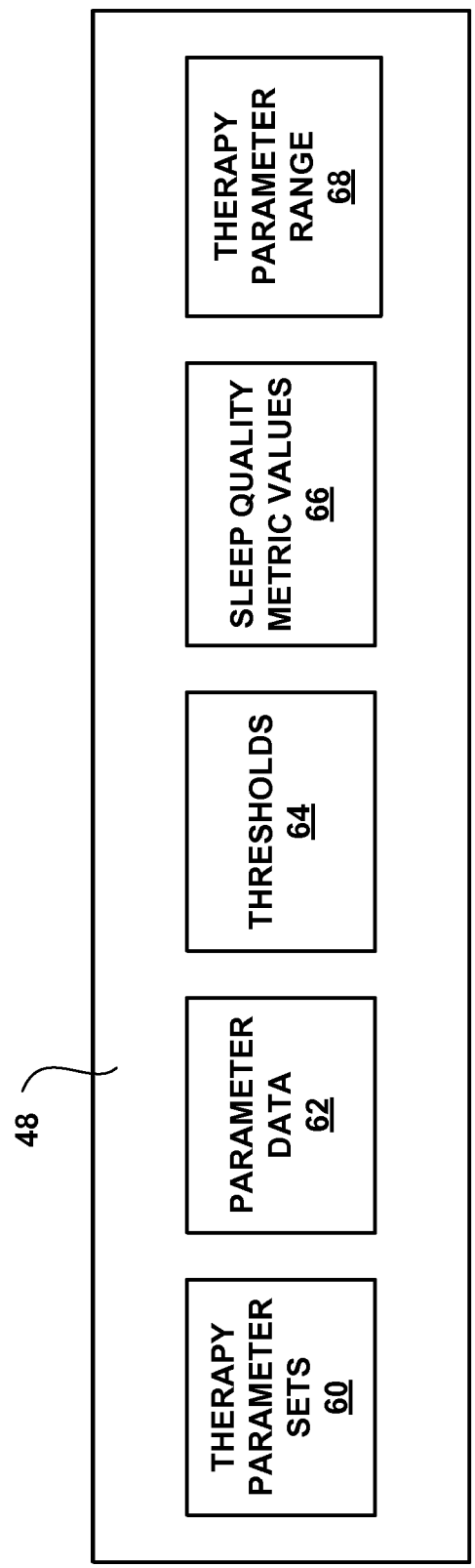
FIG. 4 is a block diagram illustrating an example memory of the implantable medical device of FIG. 1.

FIG. 4 further illustrates memory 48 of an IMD 14. As illustrated in FIG. 4, memory 48 stores a plurality of therapy parameter sets 60. Therapy parameter sets 60 may include parameter sets randomly or non-randomly generated by processor 46 over therapy parameter ranges 68 set by a clinician using clinician programmer 20. Therapy parameter sets 60 may also include parameter sets specified by a clinician using clinician programmer 20 and preprogrammed therapy parameter sets.

Memory 48 may also include parameter data 62 recorded by processor 46, e.g., physiological parameter values, or mean or median physiological parameter values. Memory 48 stores threshold values 64 used by processor 46 in the collection of sleep quality metric values, as discussed above. In some embodiments, memory 48 also stores one or more functions or look-up tables (not shown) used by processor 46 to determine sleep probability metric values, or to determine an overall sleep quality metric value.

Further, processor 46 stores determined sleep quality metric values 66 for each of the plurality of therapy parameter sets 60 within memory 48. Processor 46 conducts a sensitivity analysis of the sleep quality metric values for each therapy parameter. The sensitivity analysis determines a value for each therapy parameter that defines a substantially maximum sleep quality metric value. In other words, the sensitivity analysis identifies parameter values that yield the best sleep quality metric values. Processor 46 then determines a baseline therapy parameter set based on the sensitivity analysis and stores the baseline therapy parameter set with therapy parameter set 66 or separately within memory 48. The baseline therapy parameter set includes the values for respective parameters that produced the best sleep quality metric values.

Processor 46 may collect sleep quality metric values 66 each time a patient 12 sleeps, or only during selected times that the patient 12 is asleep. Processor 46 may store each sleep quality metric value determined within memory 48 as a sleep quality metric value 66. Further, processor 46 may apply a function or look-up table to a plurality of sleep quality metric values to determine overall sleep quality metric value, and may store the overall sleep quality metric values within memory 48. The application of a function or look-up table by processor 46 for this purpose may involve the use or weighting factors for one or more of the individual sleep quality metric values.

In some embodiments, as discussed above, processor 46 may adjust the therapy delivered by therapy module 44 based on a change in the sleep quality metric value. In particular, processor 46 may perturb one or more therapy parameters of the baseline therapy parameter set, such as pulse amplitude, pulse width, pulse rate, duty cycle, and duration to determine if the current sleep quality metric value improves or worsens during perturbation. In some embodiments, processor 46 may iteratively and incrementally increase or decrease values of the therapy parameters until a substantially maximum value of the sleep quality metric value is again determined.

Figure 5:
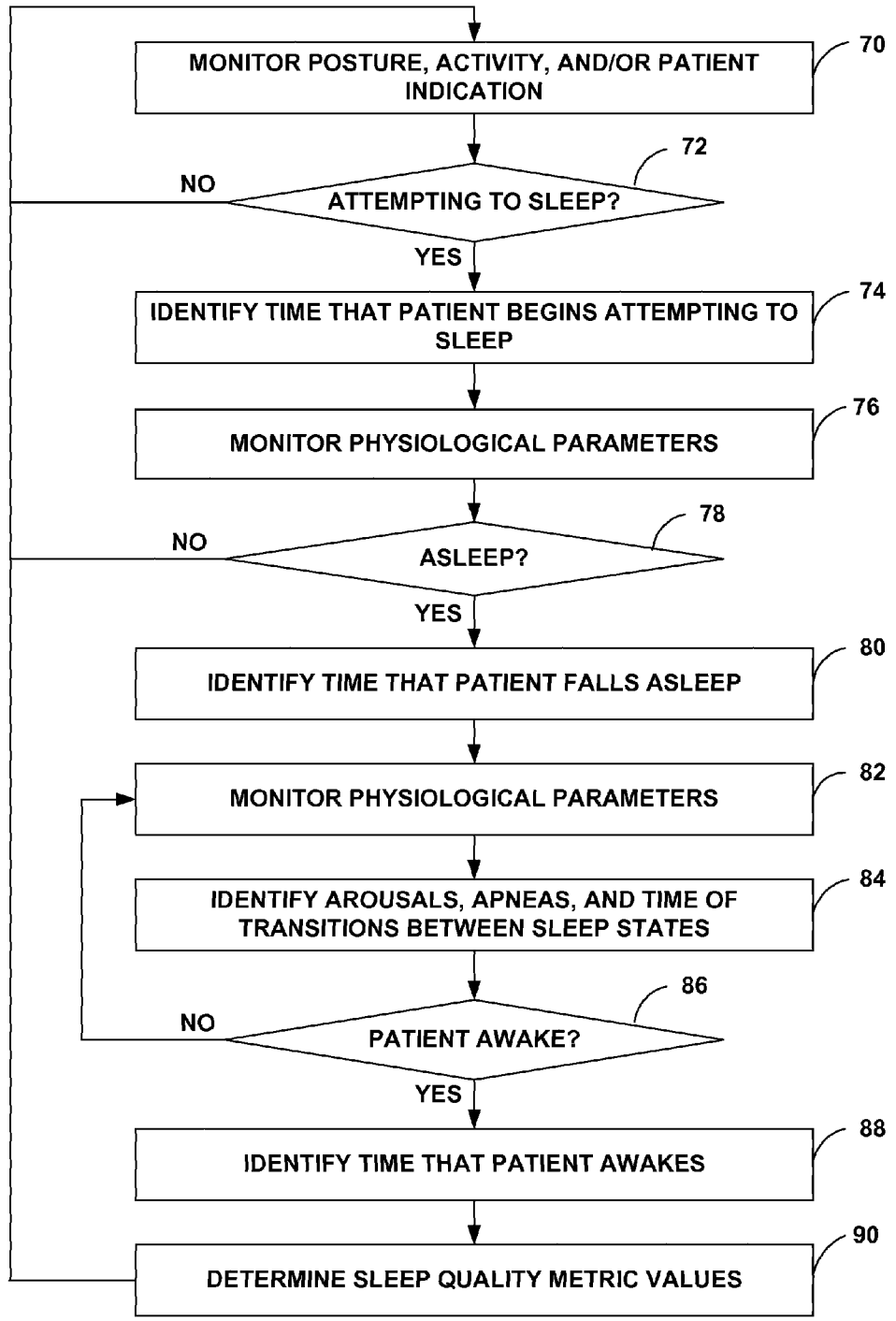
FIG. 5 is a flow diagram illustrating an example method for collecting sleep quality information that may be employed by an implantable medical device.

FIG. 5 is a flow diagram illustrating an example method for collecting sleep quality information that may be employed by an IMD 14 alone, or in combination with a computing device and/or a monitor. In some embodiments, as discussed above, a computing device, such as one of programmers 20 and 26, may determine sleep quality metric values based on monitored physiological parameter values, rather than an IMD 14. Further, in some embodiments, a monitor may monitor physiological parameter values instead or, or in addition to, an IMD 14.

In the illustrated example, however, an IMD 14 monitors the posture and/or activity level of a patient 12, or monitors for an indication from the patient 12, e.g., via patient programmer 26 (70), and determines whether the patient 12 is attempting to fall asleep based on the posture, activity level, and/or a patient indication, as described above (72). If an IMD 14 determines that a patient 12 is attempting to fall asleep, the IMD 14 identifies the time that the patient 12 began attempting to fall asleep using any of the techniques described above (74), and monitors one or more of the various physiological parameters of the patient 12 discussed above to determine whether the patient 12 is asleep (76, 78).

In some embodiments, an IMD 14 compares parameter values or parameter variability values to one or more threshold values 64 to determine whether a patient 12 is asleep. In other embodiments, an IMD 14 applies one or more functions or look-up tables to determine one or more sleep probability metric values based on the physiological parameter values, and compares the sleep probability metric values to one or more threshold values 64 to determine whether a patient 12 is asleep. While monitoring physiological parameters (76) to determine whether a patient 12 is asleep (78), an IMD 14 may continue to monitor the posture and/or activity level of the patient 12 (70) to confirm that the patient 12 is still attempting to fall asleep (72).

When an IMD 14 determines that a patient 12 is asleep, e.g., by analysis of the various parameters contemplated herein, the IMD 14 will identify the time that the patient 12 fell asleep (80). While a patient 12 is sleeping, an IMD 14 will continue to monitor physiological parameters of the patient 12 (82). As discussed above, an IMD 14 may identify the occurrence of arousals and/or apneas based on the monitored physiological parameters (84). Further, an IMD 14 may identify the time that transitions between sleep states, e.g., REM, S1, S2, S3, and S4, occur based on the monitored physiological parameters (84).

Additionally, while a patient 12 is sleeping, an IMD 14 monitors physiological parameters of the patient 12 (82) to determine whether the patient 12 has woken up (86). When an IMD 14 determines that a patient 12 is awake, the IMD 14 identifies the time that the patient 12 awoke (88), and determines sleep quality metric values based on the information collected while the patient 12 was asleep (90).

For example, one sleep quality metric value that an IMD 14 may calculate is sleep efficiency, which the IMD 14 may calculate as a percentage of time during which a patient 12 is attempting to sleep that the patient 12 is actually asleep. An IMD 14 may determine a first amount of time between the time the IMD 14 identified that a patient 12 fell asleep and the time the IMD 14 identified that the patient 12 awoke. An IMD may also determine a second amount of time between the time the IMD 14 identified that a patient 12 began attempting to fall asleep and the time the IMD 14 identified that the patient 12 awoke. To calculate the sleep efficiency, an IMD 14 may divide the first time by the second time.

Another sleep quality metric value that an IMD 14 may calculate is sleep latency, which the IMD 14 may calculate as the amount of time between the time the IMD 14 identified that a patient 12 was attempting to fall asleep and the time the IMD 14 identified that the patient 12 fell asleep. Other sleep quality metrics with values determined by an IMD 14 based on the information collected by the IMD 14 in the illustrated example include: total time sleeping per day, at night, and during daytime hours; number of apnea and arousal events per occurrence of sleep; and amount of time spent in the various sleep states. An IMD 14 may store the determined values as sleep quality metric values 66 within memory 48.

An IMD 14 may perform the example method illustrated in FIG. 5 continuously. For example, an IMD 14 may monitor to identify when a patient 12 is attempting to sleep and asleep any time of day, each day. In other embodiments, an IMD 14 may only perform the method during evening hours and/or once every N days to conserve battery and memory resources. Further, in some embodiments, an IMD 14 may only perform the method in response to receiving a command from a patient 12 or a clinician via one of programmers 20, 26. For example, a patient 12 may direct an IMD 14 to collect sleep quality information at times when the patient believes that his or her sleep quality is low or therapy is ineffective.

Figure 6:
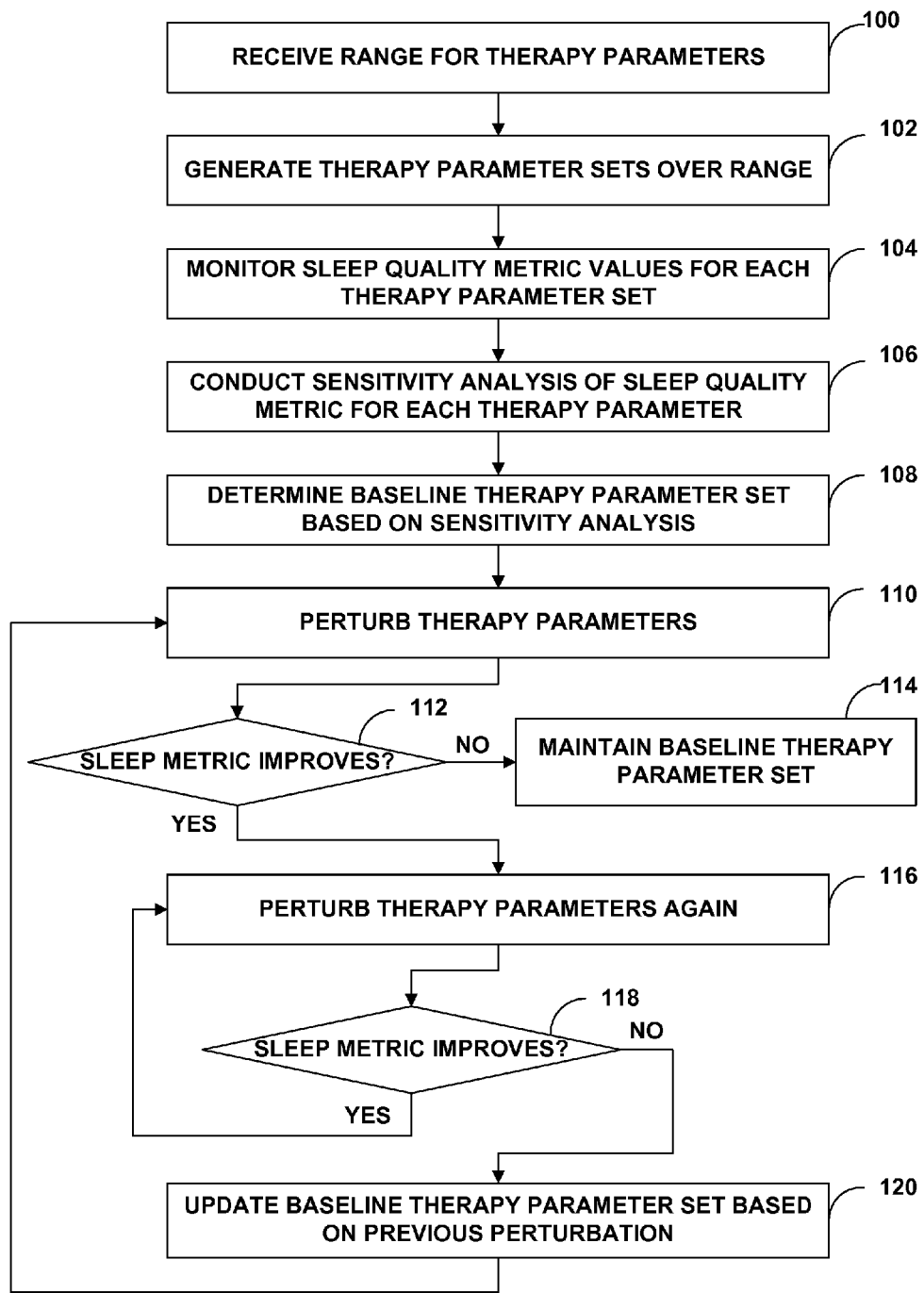
FIG. 6 is a flow diagram illustrating an example method for identifying and modifying a baseline therapy parameter set based on a sensitivity analysis of a sleep quality metric, which is an example of a performance metric.

FIG. 6 is a flow diagram illustrating an example method for identifying and modifying a baseline therapy parameter set based on a sensitivity analysis of a sleep quality metric, which is an example of a performance metric. In the illustrated example, the method is employed by an IMD 14. However, in other embodiments, a system including one or more of the IMD 14, a physiological parameter monitor, a trial therapy device, and a programmer and/or other computing device may perform the example method, as described above.

An IMD 14 receives a therapy parameter range 68 for therapy parameters (100) from a clinician using clinician programmer 20 via telemetry circuit 50. The range 68 may include minimum and maximum values for each of one or more individual therapy parameters, such as pulse amplitude, pulse width, pulse rate, duty cycle, duration, dosage, infusion rate, electrode placement, and electrode selection. Range 68 may be stored in memory 48, as described in reference to FIG. 4. Processor 46 then randomly or non-randomly generates a plurality of therapy parameter sets 60 with individual parameter values selected from the range 68 (102). The generated therapy parameter sets 60 may substantially cover range 68, but do not necessarily include each and every therapy parameter value within range 68, or every possible combination of therapy parameters within range 68. Therapy parameter sets 60 may also be stored in memory 48.

An IMD 14 monitors a sleep quality metric of a patient 12 for each of the randomly or non-randomly generated therapy parameter sets 60 spanning range 68 (104). The values of the sleep quality metric 66 corresponding to each of the therapy parameter sets 60 may be stored in memory 48 of an IMD 14. An IMD 14 then conducts a sensitivity analysis of the sleep quality metric for each of the therapy parameters (106). The sensitivity analysis determines a value for each of the therapy parameters that produced a substantially maximum value of the sleep quality metric. A baseline therapy parameter set is then determined based on the therapy parameter values from the sensitivity analysis (108). The baseline therapy parameter set includes a combination of the therapy parameter values individually observed to produce a substantially maximum sleep quality metric. In some embodiments, the patient may enter comments, a pain value from a scale, or other feedback used along with the sensitivity analysis to determine the baseline parameter set. The baseline therapy parameter set may also be stored with therapy parameters sets 60 in memory 48. In some embodiments, the baseline therapy parameter set may be stored separately from the generated therapy parameter sets.

An IMD 14 controls delivery of the therapy based on the baseline therapy parameter set. Periodically during the therapy, the IMD 14 checks to ensure that the baseline therapy parameter continues to define a substantially maximum sleep quality metric value for a patient 12. An IMD 14 first perturbs at least one of the therapy parameter values of the baseline therapy parameter set (110). The perturbation comprises incrementally increasing and/or decreasing the therapy parameter value. A perturbation period may be preset to occur at a specific time, in response to a physiological parameter monitored by the IMD, or in response to a signal from the patient or clinician. The perturbation may be applied for a single selected parameter or two or more parameters, or all parameters in the baseline therapy parameter set. Hence, numerous parameters may be perturbed in sequence. For example, upon perturbing a first parameter and identifying a value that produces a maximum metric value, a second parameter may be perturbed with the first parameter value fixed at the identified value. This process may continue for each of the parameters in the therapy parameter set.

Upon perturbing a parameter value, an IMD 14 then compares a value of the sleep quality metric defined by the perturbed therapy parameter set to the value of the sleep quality metric defined by the baseline therapy parameter set (112). If the sleep quality metric value does not improve with the perturbation, an IMD 14 maintains the unperturbed baseline therapy parameter set values (114). If the sleep quality metric value does improve with the perturbation, an IMD 14 perturbs the therapy parameter value again (116) in the same direction that defined the previous improvement in the sleep quality metric value. An IMD 14 compares a value of the sleep quality metric defined by the currently perturbed therapy parameter set and the sleep quality metric value defined by the previously perturbed therapy parameter set (118). If the sleep metric value does not improve, an IMD 14 updates the baseline therapy parameter set based on the therapy parameter values from the previous perturbation (120). If the sleep metric value improves again, an IMD 14 continues to perturb the therapy parameter value (116).

Periodically checking the value of the sleep quality metric for the baseline therapy parameter set allows an IMD 14 to consistently deliver a therapy to a patient 12 that defines a substantially maximum sleep quality metric value of the patient 12. This allows the patient's symptoms to be continually managed even as the patient's physiological parameters change.

In some embodiments, an external computing device, such as clinician programmer 20, may generate the plurality of therapy parameter sets over the range. A clinician may then provide the therapy parameter sets to an IMD 14 via clinician programmer 20. The computing device may provide individual therapy parameter sets to be tested, and may thus control the testing by an IMD 14, or may provide a listing of therapy parameter sets to be tested.

Furthermore, an external computing device, such as programmer 20, a separate desktop computer, or server, may receive the sleep quality metric values collected by the IMD for the plurality of therapy parameter sets. The external computing device may then conduct the sensitivity analysis to determine the baseline therapy parameter set. The external computing device may also control the subsequent perturbations. In some embodiments, the external computing device may receive physiological parameter values from an IMD 14, and, rather that the IMD 14, the external computing device may determine values of the sleep quality or other performance metric based on the physiological parameter values received from the IMD 14.

In some embodiments, the sensitivity analysis and determination of a baseline therapy parameter set may be performed as part of a trialing process. In such embodiments, an external or implanted trial therapy device, such as a trial neurostimulator, may perform the functions ascribed to an IMD 14 above that are associated with performing the sensitivity analysis and determination of a baseline therapy parameter set. The trial therapy device may include a therapy module 44, processor 46, and memory 48, and may be coupled to sensors 40 and leads 16, as described above with reference to an IMD 14 and FIGS. 2A, 2B and 4.

An IMD 14 may then be implanted in a patient 12, and programmed to deliver therapy according to the baseline therapy parameter set. In such embodiments, an IMD 14 may perform the perturbation and updating functions of the example method illustrated by FIG. 6. In some embodiments, an external computing device may control delivery of a plurality of therapy parameter sets by the trial device, determine performance metric values based on physiological parameter values received from the trial device, and/or perform the sensitivity analysis.

Figure 7:
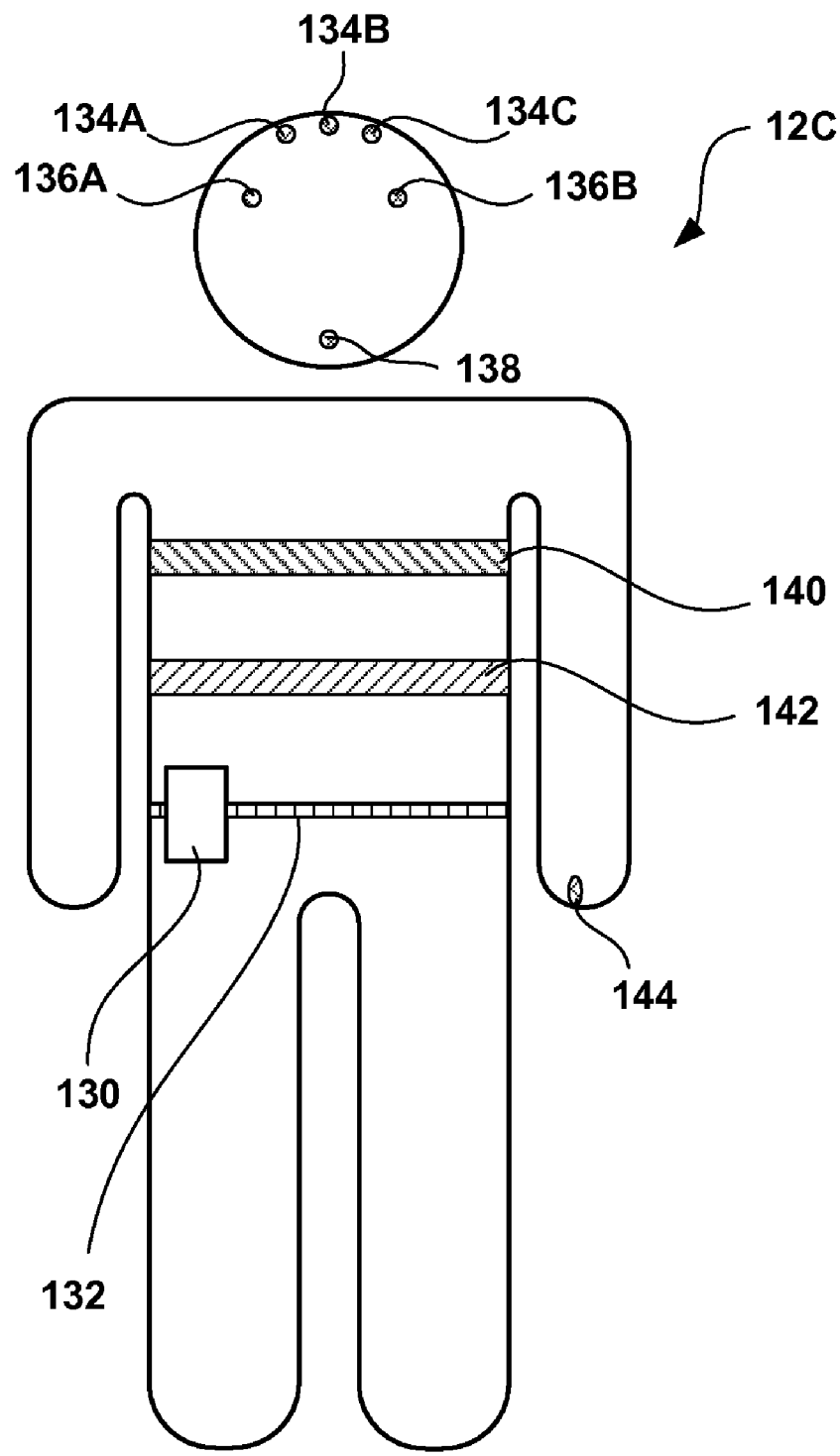
FIG. 7 illustrates, a separate monitor that monitors values of one or more physiological parameters of a patient instead of, or in addition to therapy delivering medical device.

FIG. 7 illustrates a separate monitor 130 that monitors values of one or more physiological parameters of patient 12C instead of, or in addition to the trial device or an IMD 14. Monitor 130 may include a processor 46 and memory 48, and may be coupled to sensors 40, as illustrated above with reference to an IMD 14 and FIGS. 2A, 2B and 4. Monitor 130 may identify performance metric values based on the values of the monitored physiological parameter values, or may transmit the physiological parameter values to a computing device for determination of the performance metric values. In some embodiments, an external computing device, such as a programming device, may incorporate monitor 130. In the illustrated embodiment, monitor is configured to be attached to or otherwise carried by a belt 132, and may thereby be worn by patient 12C.

FIG. 7 also illustrates various sensors 40 that may be coupled to monitor 130 by leads, wires, cables, or wireless connections, such as EEG electrodes 134A-C placed on the scalp of patient 12C, a plurality of EOG electrodes 136A and 136B placed proximate to the eyes of patient 12C, and one or more EMG electrodes 138 placed on the chin or jaw the patient. The number and positions of electrodes 134, 136 and 138 illustrated in FIG. 7 are merely exemplary. For example, although only three EEG electrodes 134 are illustrated in FIG. 7, an array of between 16 and 25 EEG electrodes 134 may be placed on the scalp of patient 12C, as is known in the art. EEG electrodes 134 may be individually placed on patient 12C, or integrated within a cap or hair net worn by the patient. Monitor 130 may include an EEG module 49 or similar to determine sleep states in some examples.

In the illustrated example, patient 12C wears an ECG belt 140. ECG belt 140 incorporates a plurality of electrodes for sensing the electrical activity of the heart of patient 12C. The heart rate and, in some embodiments, ECG morphology of patient 12C may monitored by monitor 130 based on the signal provided by ECG belt 140. Examples of suitable belts 140 for sensing the heart rate of patient 12C are the "M" and "F" heart rate monitor models commercially available from Polar Electro. In some embodiments, instead of belt 140, patient 12C may wear a plurality of ECG electrodes attached, e.g., via adhesive patches, at various locations on the chest of the patient, as is known in the art. An ECG signal derived from the signals sensed by such an array of electrodes may enable both heart rate and ECG morphology monitoring, as is known in the art.

As shown in FIG. 7, patient 12C may also wear a respiration belt 142 that outputs a signal that varies as a function of respiration of the patient. Respiration belt 142 may be a plethysmograpy belt, and the signal output by respiration belt 142 may vary as a function of the changes is the thoracic or abdominal circumference of patient 12C that accompany breathing by the patient. An example of a suitable belt 142 is the TSD201 Respiratory Effort Transducer commercially available from Biopac Systems, Inc. Alternatively, respiration belt 142 may incorporate or be replaced by a plurality of electrodes that direct an electrical signal through the thorax of the patient, and circuitry to sense the impedance of the thorax, which varies as a function of respiration of the patient, based on the signal. In some embodiments, ECG and respiration belts 140 and 142 may be a common belt worn by patient 12C, and the relative locations of belts 140 and 142 depicted in FIG. 7 are merely exemplary.

In the example illustrated by FIG. 7, patient 12C also wears a transducer 144 that outputs a signal as a function of the oxygen saturation of the blood of patient 12C. Transducer 144 may be an infrared transducer. Transducer 144 may be located on one of the fingers or earlobes of patient 12C. Sensors 40 coupled to monitor 130 may additionally or alternatively include any of the variety of sensors described above that monitor any one or more of activity level, posture, heart rate, ECG morphology, EEG morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response. Signals received from EEG electrodes 174A-C may be analyzed to determine sleep states, e.g., using techniques and circuitry described with reference to FIG. 3.

FIG. 7 also illustrates an external trial therapy device 146 in conjunction with patient 12C. In the illustrated example, patient 12C wears trial therapy device 146 with monitor 130 on belt 132. The trial therapy device 146 may be coupled to one or more transcutaneoulsy implanted leads or catheters for delivery of therapy, such as neurostimulation or a drug, to patient 12C. As described above, trial therapy device 146 may deliver therapy to patient 12C during the sensitivity analysis and baseline therapy parameter set determination portion of the method illustrated in FIG. 6 and, in some embodiments, may also monitor physiological parameters of patient 12C, determine performance metric values, and/or perform the sensitivity analysis to determine the baseline therapy parameter set for use by an IMD 14.

Figure 8:
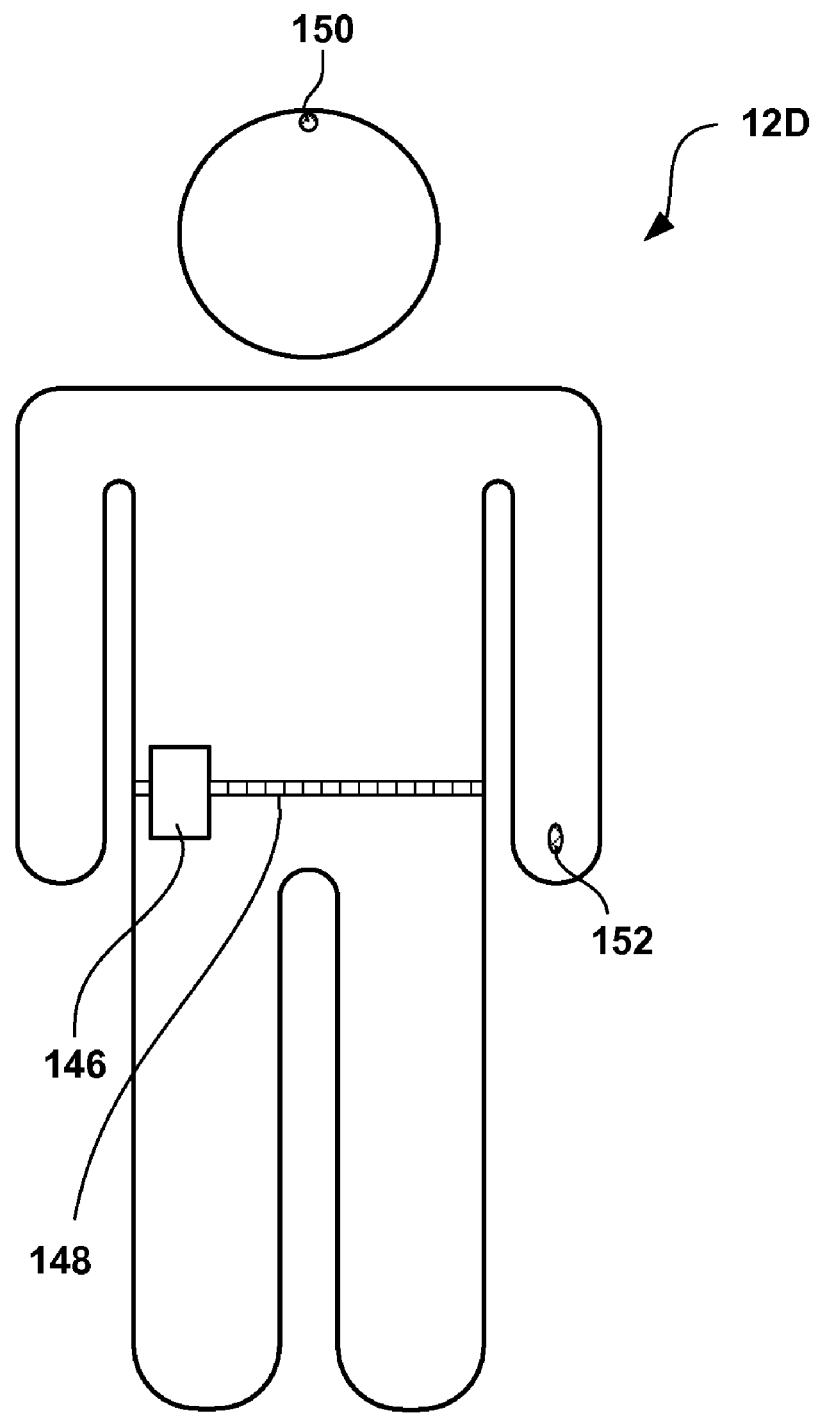
FIG. 8 is a conceptual diagram illustrating a monitor that monitors signals generated by one or more accelerometers disposed on the patient.

FIG. 8 is a conceptual diagram illustrating a monitor that monitors signals generated by one or more accelerometers instead of, or in addition to, such monitoring of signals generated by accelerometers or other sensors by a therapy delivering medical device. As shown in FIG. 8, patient 12D is wearing monitor 146 attached to belt 148. Monitor 146 is capable of receiving measurements from one or more sensors located on or within patient 12D. In the example of FIG. 8, accelerometers 150 and 152 are attached to the head and hand of patient 12D, respectively. Accelerometers 150 and 152 may measure movement of the extremities, or activity level, of patient 12D to indicate when the patient moves during sleep or at other times during the day. Alternatively, more or less accelerometers or other sensors may be used with monitor 146.

Accelerometers 150 and 152 may be preferably multi-axis accelerometers, but single-axis accelerometers may be used. As patient 12D moves, accelerometers 150 and 152 detect this movement and send the signals to monitor 146. High frequency movements of patient 12D may be indicative of tremor, Parkinson's disease, or an epileptic seizure. Accelerometers 150 and 152 may be worn externally, i.e., on a piece or clothing or a watch, or implanted at specific locations within patient 12D. In addition, accelerometers 150 and 152 may transmit signals to monitor 146 via a wireless or a wired connection.

Monitor 146 may store the measurements from accelerometers 150 and 152 in a memory. In some examples, monitor 146 may transmit the measurements from accelerometers 150 and 152 directly to another device, such as an IMD 14 or a programmer. In this case, an the IMD 14 or programmer may analyze the measurements from accelerometers 150 and 152 to detect efficacy of therapy, control the delivery of therapy, detect sleep or monitor sleep quality using any of the techniques described herein.

In some examples, a rolling window of time may be used when analyzing measurements from accelerometers 150 and 152. Absolute values determined by accelerometers 150 and 152 may drift with time or the magnitude and frequency of patient 12D movement may not be determined by a preset threshold. For this reason, it may be advantageous to normalize and analyze measurements from accelerometers 150 and 152 over a discrete window of time. For example, the rolling window may be useful in detecting epileptic seizures. If monitor 146 or an IMD 14 detects at least a predetermined number of movements over a 15 second window, an epileptic seizure may be most likely occurring. In this manner, a few quick movements from patient 12D not associated with a seizure may not trigger a response, such as recording an incident in a memory or a change in therapy.

Figure 9:
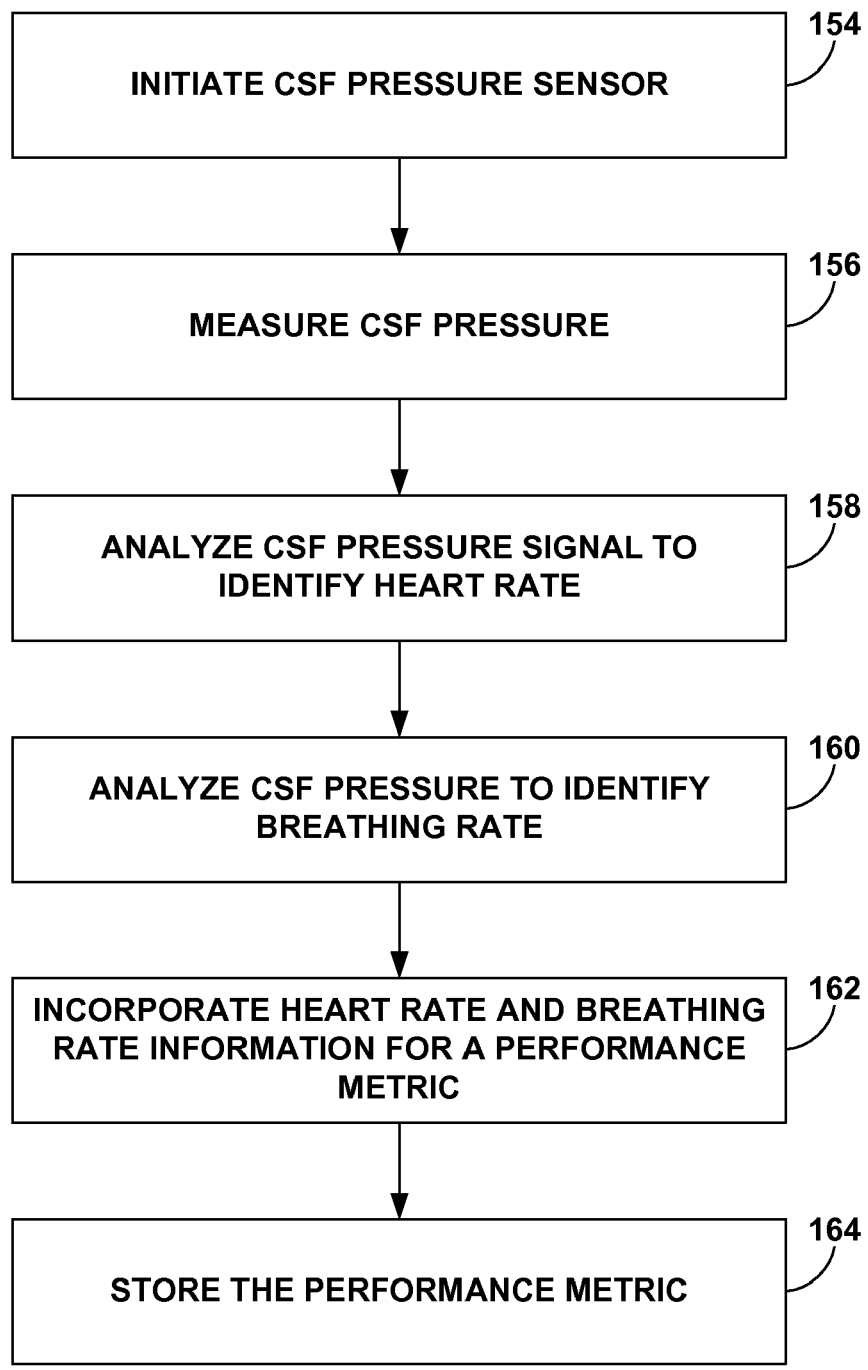
FIG. 9 is a flow diagram illustrating an example technique for monitoring the heart rate and breathing rate of a patient by measuring cerebral spinal fluid pressure.

FIG. 9 is a flow diagram illustrating monitoring the heart rate and breathing rate of a patient by measuring cerebral spinal fluid pressure. As discussed above, a physiological parameter that may be measured in a patient 12 is heart rate and respiration, or breathing, rate. In the example of FIG. 9, cerebral spinal fluid (CSF) pressure may be analyzed to monitor the heart rate and breathing rate of a patient 12. A clinician initiates a CSF pressure sensor for monitoring heart rate and/or breathing rate (154). Alternatively, the CSF pressure sensor may be implanted within the brain or spinal cord of patient 12 to acquire accurate pressure signals. The CSF pressure sensor may transfer pressure data to an implanted or external device. As an example used herein, the CSF pressure sensor transmits signal data to an IMD 14.

Once the CSF pressure sensor is initiated, the CSF pressure sensor measures CSF pressure and transmits the data to an IMD 14 (156). IMD 14 analyzes the CSF pressure signal to identify the heart rate (158) and breathing rate (160) of a patient 12. The heart rate and breathing rate can be identified within the overall CSF pressure signal. Higher frequency fluctuations (e.g. 40 to 150 beats per minute) can be identified as the heart rate while lower frequency fluctuations (e.g. 3 to 20 breaths per minute) in CSF pressure are the breathing rate. An IMD 14 may employ filters, transformations, or other signal processing techniques to identify the heart rate and breathing rate from the CSF pressure signal.

An IMD 14 may utilize the heart rate and breathing rate information when determining when a patient 12 is attempting to sleep, determining when the patient 12 is asleep, identifying patient activity, or otherwise determining a performance metric for determining a sensitivity analysis for the patient 12, as described above (162). For example, faster heart rates and faster breathing rates may indicate that patient 12 is active and not sleeping. An IMD 14 may then store values of the performance metric, provide the analysis to a programmer or other computing device, or use them to adjust stimulation therapy (164).

Various embodiments of the invention have been described. However one skilled in the art will appreciate that various modifications may be made to the described embodiments without departing from the scope of the invention. For example, although described herein primarily in the context of treatment with an implantable neurostimulator or implantable pump, the invention is not so limited. Moreover, the invention is not limited to implantable medical devices. The invention may be embodied in any implantable or external medical device that delivers therapy to treat any ailment of symptom of a patient.

As another example, the invention has been primarily described in the context of monitoring a sleep quality metric; however the invention is not so limited. The invention may monitor any performance metric, such as an activity metric, posture metric, a movement disorder metric, or other metrics that indicate the efficacy or degree of side effects associated a therapy delivered to a patient.

In some embodiments, for example, IMD 14 or any of the other devices described herein may periodically determine an activity level of patient 12 during delivery of therapy to the patient according to a plurality of parameter sets by monitoring at least one signal that is generated by a sensor 40 and varies as a function of patient activity, as described above. A value of at least one activity metric for each of a plurality of therapy parameter sets may be determined based on the activity levels associated with that parameter set. An activity metric value may be, for example, a mean or median activity level, such as an average number of activity counts per unit time. In other embodiments, an activity metric value may be chosen from a predetermined scale of activity metric values based on comparison of a mean or median activity level to one or more threshold values. The scale may be numeric, such as activity metric values from 1-10, or qualitative, such as low, medium or high activity.

In some embodiments, each activity level associated with a therapy parameter set is compared with the one or more thresholds, and percentages of time above and/or below the thresholds are determined as one or more activity metric values for that therapy parameter set. In other embodiments, each activity level associated with a therapy parameter set is compared with a threshold, and an average length of time that consecutively determined activity levels remain above the threshold is determined as an activity metric value for that therapy parameter set. One or both of the medical device or a programming device may determine the activity metric values as described herein.

As another example, the device may monitor one or more signals that are generated by respective sensors 40 and vary as a function of patient posture, as described above. Posture events are identified based on the posture of the patient, e.g., the patient's posture and/or posture transitions are periodically identified, and each identified posture event is associated with the current therapy parameter set.

A value of at least one posture metric is determined for each of the therapy parameter sets based on the posture events associated with that parameter set. A posture metric value may be, for example, an amount or percentage of time spent in a posture while a therapy parameter set is active, e.g., average amount of time over a period of time, such as an hour, that a patient was within a particular posture. In some embodiments, a posture metric value may be an average number of posture transitions over a period of time, e.g., an hour, that a particular therapy parameter sets was active.

In embodiments in which a plurality of posture metrics are determined for each therapy parameter set, an overall posture metric may be determined based on the plurality of posture metrics. The plurality of posture metrics may be used as indices to select an overall posture metric from a look-up table comprising a scale of potential overall posture metrics. The scale may be numeric, such as overall posture metric values from 1-10.

Similarly, a device may sense physiological parameter values of a patient indicative of movement disorders, such as tremor, via one or more sensors 40, such as one or more accelerometers. Movement disorder metrics values that may be determined include mean or median values output by the sensors, amounts of time the sensor signal is above or below a threshold, or frequency of episodes above or below a threshold.

The overall activity level of a patient, e.g., the extent to which the patient is on his or her feet and moving or otherwise active, rather than sitting or lying in place, may be negatively impacted by any of a variety of ailments or symptoms. Accordingly, the activity level of a patient may reflect the efficacy of a particular therapy or therapy parameter set in treating the ailment or symptom. In other words, it may generally be the case that the more efficacious a therapy parameter set is, the more active and upright the patient will be.

In accordance with the invention, activity levels, postures, particular symptomatic activities or postures, and/or sleep quality may be monitored during delivery of therapy according to a plurality of therapy parameter sets, and used to evaluate the efficacy of the therapy parameter sets. As an example, chronic pain may cause a patient to avoid particular activities, high levels of activity, or activity in general. Systems according to the invention may include any of a variety of medical devices that deliver any of a variety of therapies to treat chronic pain, such as SCS, DBS, cranial nerve stimulation, peripheral nerve stimulation, or one or more drugs. Systems may use the techniques of the invention described above to associate activity levels and metrics with therapy parameter sets for delivery of such therapies, and thereby evaluate the extent to which a therapy parameter set is alleviating chronic pain by evaluating the extent to which the therapy parameter set improves the overall activity level, posture and sleep quality of the patient.

As another example, psychological disorders may cause a patient to experience low sleep quality and, particularly in the case of depression, be less active. Accordingly, embodiments of the invention may determine sleep quality and activity metrics to track the status or progression of a psychological disorder, such as depression, mania, bipolar disorder, or obsessive-compulsive disorder. Further, systems according to the invention may include any of a variety of medical devices that deliver any of a variety of therapies to treat a psychological disorder, such as DBS, cranial nerve stimulation, peripheral nerve stimulation, vagal nerve stimulation, or one or more drugs. Systems may use the techniques of the invention described above to associate sleep quality and activity metric values with the therapies or therapy parameter sets for delivery of such therapies, and thereby evaluate the extent to which a therapy or therapy parameter set is alleviating the psychological disorder by evaluating the extent to which the therapy parameter set improves the sleep quality of the patient, and the activity level of the patient.

Movement disorders, such as tremor, Parkinson's disease, multiple sclerosis, and spasticity may also affect the sleep quality experienced by a patient. The uncontrolled movements, e.g., tremor or shaking, associated such disorders, particularly in the limbs, may cause a patient to experience disturbed sleep. Accordingly, systems according to the invention may monitor sleep quality metrics to determine the state or progression of a movement disorder.

Movement disorders, such as tremor, Parkinson's disease, multiple sclerosis, and spasticity may also affect the overall activity level of a patient. Further, movement disorders are also characterized by irregular, uncontrolled and generally inappropriate movements, e.g., tremor or shaking, particularly of the limbs. In addition to using the sensors described above to sense the overall activity level of a movement disorder patient, some embodiments of the invention may use such sensors to detect the types of inappropriate movements associated with the movement disorder. For example, accelerometers, piezoelectric crystals, or EMG electrodes located in the trunk or limbs of a patient may be able to detect inappropriate movements such as tremor or shaking.

Systems according to the invention may periodically determine the level or severity of such movements based on the signals output by such sensors, associate the inappropriate movement levels with current therapy parameter sets, and determine activity metric values for therapy parameter sets based on the associated levels. For example, a processor of such a system may determine a frequency or amount of time that such movements exceeded a threshold during delivery of a therapy parameter set as an inappropriate movement based activity metric value for the therapy parameter set.

Another activity-related movement disorder symptom that is relatively specific to Parkinson's disease is "gait freeze." Gait freeze may occur when a Parkinson's patient is walking. Gait freeze refers to a relatively sudden inability of a Parkinson's patient to take further steps. Gait freeze is believed to result from a neurological failure and, more specifically, a failure in the neurological signaling from the brain to the legs.

In some embodiments, in addition to the activity metrics described above, any of the devices or processors described above may additionally identify gait freeze events based on the signals output by sensors 40. For example, processor 46, or another processor of the system, may detect a relatively sudden cessation of activity associated with a gait event based on the output of accelerometers, piezoelectric crystals, EMG electrodes, or other sensors that output signals based on footfalls or impacts associated with, for example, walking. When experiencing a gait freeze event, a patient may "rock" or "wobble" while standing in place, as if attempting unsuccessfully to move. In some embodiments, processor 46 may monitor any of sensors 40 that output signals as a function of posture discussed above, such as a 3-axis accelerometer, to detect the minor, rhythmic changes in posture associated with rocking or wobbling. Processor 46 may detect a gait freeze event as when it occurs based on one or more of the posture or activity sensors. For example, processor 46 may confirm that a relatively sudden cessation of activity is in fact a gait freeze event based on rocking or wobbling indicated by posture sensors.

In some embodiments, the processor may detect a gait freeze prior to onset. For example, sensors 40 may include EMG or EEG electrodes, and processor 46 may detect a gait freeze prior to onset based on irregular EMG or EEG activity. EMG signals, as an example, demonstrate irregularity just prior to a freezing episode, and a processor may detect this irregularity as being different from the EMG signals typically associated with walking. In other words, a walking patient may exhibit normal EMG pattern in the legs, which may be contrasted with EMG activity and timing changes that precede freezing.

In general, EMG signals from right and left leg muscles include a regularly alternating rhythm pattern that characterizes normal gait. When the "timing" of the pattern fails, there is no longer a regular rhythm, and a gait freeze may result. Accordingly, a processor may detect irregularity, variability, or asymmetry, e.g., within and between right and left leg muscles, in one or more EMG signals, and may detect an oncoming gait freeze prior to occurrence based on the detection. In some embodiments, the processor may compare the EMG signals to one or more thresholds to detect gait freeze. Comparison to a threshold may, for example, indicate an absolute value or increase in irregularity, variability, asymmetry that exceeds a threshold, indicating an oncoming gait freeze. In some embodiments, thresholds may be determined based on EMG signal measurements made when the patient is walking normally.

Whether or not gait freeze is detected prior to r during occurrence, the processor may associate the occurrence of the gait freeze event with a current therapy parameter set used to control delivery of a therapy for Parkinson's disease, such as DBS or a drug. Additionally, the processor may determine or update an activity metric value for the therapy parameter set based on the gait freeze event, such as a total number of gait freeze events for the therapy parameter set, or an average number of gait freeze events over a period of time.

Systems according to the invention may include any of a variety of medical devices that deliver any of a variety of therapies to treat movement disorders, such as DBS, cortical stimulation, or one or more drugs. Baclofen, which may or may not be intrathecally delivered, is an example of a drug that may be delivered to treat movement disorders. Systems may use the techniques of the invention described above to associate any of the above-described sleep quality or activity metrics with therapies or therapy parameter sets for delivery of such therapies. In this manner, such systems may allow a user to evaluate the extent to which a therapy or therapy parameter set is alleviating the movement disorder by evaluating the extent to which the therapy parameter set improves the sleep quality, general activity level, inappropriate activity level, or number of gait freezes experienced by the patient.

Further, many of the ailments and symptoms described above, including movement disorders and chronic pain, may affect the gait of a patient. More particularly, such symptoms and ailments may result in, as examples, an arrhythmic, asymmetric (left leg versus right leg), or unusually variable gait, or a gait with relative short stride lengths. Systems according to the invention may use sensors discussed above that output signals as a function of activity, and particularly as a function of footfalls or impacts, to monitor gait.

For example, a processor of such a system may periodically determine a value for asymmetry, variability, or stride length of gait, and associated such values with a current therapy parameter set used deliver any of the therapies discussed herein with reference to chronic pain or movement disorders. The processor may determine an activity metric value based on gait by, for example, averaging the gait values associated with a therapy parameter set over a period of time, such as a day, week or month. The processor of the system that performs the techniques of the invention, such as gait monitoring and activity metric determination, may include one or more of a processor of an IMD or a processor of a programming or computing device, as discussed above.

Many of the above metrics, including overall activity and gait-related metrics, are activity-related performance metrics that may be particularly relevant to evaluating chronic pain, movement disorders, psychological disorders, and their therapies. Further details regarding activity and posture metric values may be found in U.S. patent application Ser. No. 11/691,411, by Ken Heruth and Keith Miesel, entitled "COLLECTING ACTIVITY INFORMATION TO EVALUATE THERAPY," filed on Mar. 26, 2007, and U.S. patent application Ser. No. 11/691,391, by Ken Heruth and Keith Miesel, entitled "COLLECTING POSTURE INFORMATION TO EVALUATE THERAPY," filed on Mar. 26, 2007. The content of these applications is incorporated herein by reference in its entirety.

Additionally, as discussed above, feedback entered by patient 12, may be used as a performance metric instead of, or in addition to, the other performance metrics described herein. One of programming devices 20, 26 may receive the feedback from patient 12. In embodiments in which another device, such as a medical device or other computing device, performs the sensitivity analysis, the programming device may provide the feedback or performance metric values derived from the feedback to the other device. As examples, the feedback may include comments, or numeric values for pain, efficacy, or side effect levels.

For example, the programming device 20, 26 may prompt patient 12 for feedback after a new or modified program is delivered by a therapy delivering medical device during the sensitivity analysis or perturbation portions of the method illustrated by FIG. 6. Additionally or alternatively, if patient 12 experiences discomfort, the patient could cause the sensitivity analysis or perturbation to "step backward" to the most recent setting before the setting was changed by the algorithm via the programming device. When the patient causes the algorithm to step backward, the device performing the sensitivity analysis or perturbation may record this as a low performance metric value for the avoided program, or may prevent further program testing, perturbation, or other program selection of the avoided program, or within in a zone of therapy parameters determined based on the avoided program. In embodiments in which feedback is used in addition to one or more other performance metrics, a clinician or physician may determine a weighting scheme to provide more or less significance to the patient's feedback, i.e., the physician may choose to give the patient feedback zero weight and instead rely completely on other performance metric values, or the physician may judge that the patient has enough perspective to be able to competently gage pain levels and input substantially objective feedback into the sensitivity analysis.

These and other embodiments are within the scope of the following claims.

The invention claimed is:

1. A method comprising:
delivering at least one of a movement disorder therapy, psychological disorder therapy, or deep brain stimulation therapy to a patient via a medical device according to each of a plurality of therapy parameter sets, each of the parameter sets including a value for each of a plurality of therapy parameters;
monitoring a value of a performance metric of the patient for each of the plurality of therapy parameter sets;
conducting a sensitivity analysis of the performance metric for each of the plurality of therapy parameters based on the monitored values of the performance metric; and
identifying a value for each of the therapy parameters based on the sensitivity analysis,
wherein the performance metric comprises a sleep quality metric.

2. The method of claim 1, further comprising receiving a range for at least one therapy parameter in the therapy parameter sets and generating the plurality of therapy parameter sets with different values of the therapy parameter distributed over the range.

3. The method of claim 1, wherein identifying a value comprises identifying a value corresponding to one of a maximum value and a minimum value of the performance metric.

4. The method of claim 1, further comprising delivering the therapy to the patient based on a baseline therapy parameter set that includes the identified values.

5. The method of claim 4, wherein delivering the therapy to the patient based on a baseline therapy parameter set comprises delivering the therapy to the patient via one of the medical device or another medical device.

6. The method of claim 4, further comprising perturbing at least one therapy parameter of the baseline therapy parameter set, monitoring a perturbed value of the performance metric in response to the perturbed therapy parameter, comparing the perturbed value of the performance metric to the value of the performance metric for the baseline therapy parameter set and adjusting the therapy based on the comparison.

7. The method of claim 1, further comprising determining the sleep quality metric by:
monitoring a frequency of an electroencephalogram (EEG) signal;
identifying a sleep state based on the frequency of the EEG signal; and
determining the sleep quality metric based on the sleep state.

8. The method of claim 1, wherein the performance metric comprises a patient feedback metric.

9. The method of claim 1, wherein the performance metric comprises at least one of an activity level metric or a posture metric.

10. The method of claim 1, wherein the performance metric comprises at least one of a movement disorder metric or a side-effects metric.

11. A medical device comprising:
a therapy module to deliver at least one of a movement disorder therapy, psychological disorder therapy, or deep brain stimulation to a patient according to each of a plurality of therapy parameter sets, each of the therapy parameter sets including a value for each of a plurality of therapy parameters; and
a processor to monitor a value of a performance metric of the patient for each of the plurality of therapy parameter sets, conduct a sensitivity analysis of the performance metric for each of the plurality of therapy parameters based on the monitored values of the performance metric, and identify a value for each of the therapy parameters based on the sensitivity analysis, wherein the processor monitors a sleep quality metric.

12. The medical device of claim 11, further comprising telemetry circuitry to receive a range for at least one therapy parameter in the therapy parameter sets, wherein the processor generates the plurality of therapy parameter sets with different values of the therapy parameter distributed over the range.

13. The medical device of claim 11, further comprising a memory to store a range for at least one therapy parameter in the therapy parameter sets, wherein the processor generates the plurality of therapy parameter sets with different values of the therapy parameter distributed over the range and stores the plurality of therapy parameter sets in the memory.

14. The medical device of claim 11, wherein the processor controls delivery of the therapy by the therapy module based on a baseline therapy parameter set that includes the identified values.

15. The medical device of claim 14, wherein the processor perturbs at least one therapy parameter of the baseline therapy parameter set, monitors a perturbed value of the performance metric in response to the perturbed therapy parameter, compares the perturbed value of the performance metric to the value of the performance metric for the baseline therapy parameter set and adjusts the therapy based on the comparison.

16. The medical device of claim 11, wherein the processor:
monitors a frequency of an electroencephalogram (EEG) signal;
identifies a sleep state based on the frequency of the EEG signal; and
determines the sleep quality metric based on the sleep state.

17. The medical device of claim 11, wherein the performance metric comprises a patient feedback metric.

18. The medical device of claim 11, wherein the medical device comprises an implantable medical device.

19. The medical device of claim 11, wherein the medical device comprises at least one of a neurostimulator or a pump.

20. The medical device of claim 11, wherein the medical device comprises at least one of a trial neurostimulator or a trial pump.

21. The medical device of claim 11, wherein the medical device delivers the therapy to the patient to treat chronic pain.

22. The medical device of claim 11, wherein the performance metric comprises at least one of an activity level metric or a posture metric.

23. The medical device of claim 11, wherein the performance metric comprises at least one of a movement disorder metric or a side-effects metric.

24. A non-transitory computer-readable medium comprising instructions that cause a programmable processor to:
monitor a value of a performance metric of a patient for each of a plurality of therapy parameter sets, wherein a medical device delivers at least one of a movement disorder therapy, psychological disorder therapy, or deep brain stimulation to the patient according to each of the therapy parameter sets, and each of the parameter sets includes a value for each of a plurality of therapy parameters;
conduct a sensitivity analysis of the performance metric for each of the plurality of therapy parameters based on the monitored values of the performance metric; and
identify a value for each of the plurality of therapy parameters based on the sensitivity analysis,
wherein the performance metric comprises a sleep quality metric.

25. The medium of claim 24, further comprising instructions that cause the processor to receive a range for at least one therapy parameter in the therapy parameter sets and generate the plurality of therapy parameter sets with different values of the therapy parameter distributed over the range.

26. The medium of claim 24, further comprising instructions that cause the processor to perturb at least one therapy parameter of a baseline therapy parameter set that includes the identified therapy parameter values, monitor a perturbed value of the performance metric in response to the perturbed therapy parameter, compare the perturbed value of the performance metric to the value of the performance metric for the baseline therapy parameter set and adjust the therapy based on the comparison.

27. The medium of claim 24, wherein the performance metric comprises a patient feedback metric.

28. The medium of claim 24, wherein the performance metric comprises at least one of an activity level metric or a posture metric.

29. The medium of claim 24, wherein the performance metric comprises at least one of a movement disorder metric or a side-effects metric.

30. A system comprising:
a therapy device that delivers at least one of a movement disorder therapy, psychological disorder therapy, or deep brain stimulation to a patient according to each of a plurality of therapy parameter sets, each of the therapy parameter sets including a value for each of a plurality of therapy parameters;
a monitor that monitors values of at least one physiological parameter of a patient for each of the plurality of therapy parameter sets; and
a computing device that receives the physiological parameter values from the monitor, identifies a value of a performance metric of the patient for each of the plurality of parameter sets based on the physiological parameter values, conducts a sensitivity analysis of the performance metric for each of the plurality of therapy parameters based on the monitored values of the performance metric, and identifies a value for each of the therapy parameters based on the sensitivity analysis,
wherein the performance metric comprises a sleep quality metric.

31. The system of claim 30, wherein one of the therapy device and the computing device comprises the monitor.

32. The system of claim 30, wherein the computing device comprises a programming device.

33. The system of claim 30, wherein the computing device receives a range for at least one therapy parameter in the therapy parameter sets and generates the plurality of therapy parameter sets with different values of the therapy parameter distributed over the range.

34. The system of claim 30, wherein the computing device conducts the sensitivity analysis to determine a value for at least one therapy parameter corresponding to one of a maximum value and a minimum value of the performance metric.

35. The system of claim 30, wherein one of the therapy device or another therapy device receives a baseline therapy parameter set that includes the identified values from the computing device, and delivers the therapy to the patient according to the baseline therapy parameter set.

36. The system of claim 35, wherein the computing device directs the therapy device or the other therapy device to perturb at least one therapy parameter of the baseline therapy parameter set and monitors a perturbed value of the performance metric in response to the perturbed therapy parameter.

37. The system of claim 36, wherein the computing device compares the perturbed value of the performance metric to the value of the performance metric for the baseline therapy parameter set and updates the baseline therapy parameter set based on the comparison, and one of the therapy device or the other therapy device receives the updated baseline therapy parameter set from the computing device to adjust the therapy based on the updated baseline therapy parameter set.

38. The system of claim 30, wherein the computing device:
monitors a frequency of an electroencephalogram (EEG) signal;
identifies a sleep state based on the frequency of the EEG signal; and
determines the sleep quality metric based on the sleep state.

39. The system, of claim 30, wherein the performance metric comprises a patient feedback metric.

40. The system of claim 30, wherein the therapy device comprises an implantable medical device.

41. The system of claim 30, wherein the therapy device comprises at least one of a neurostimulator or a pump.

42. The system of claim 30, wherein the therapy device comprises at least one of a trial neurostimulator or a trial pump.

43. The system of claim 30, wherein the performance metric comprises at least one of an activity level metric or a posture metric.

44. The system of claim 30, wherein the performance metric comprises at least one of a movement disorder metric or a side-effects metric.

* * * * *